(12) United States Patent
Ghovanloo et al.

(10) Patent No.: US 8,774,291 B2
(45) Date of Patent: Jul. 8, 2014

(54) PULSE HARMONIC MODULATION SYSTEMS AND METHODS

(75) Inventors: Maysam Ghovanloo, Atlanta, GA (US); Farzad Inanlou, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 88 days.

(21) Appl. No.: 13/521,123

(22) PCT Filed: Dec. 9, 2010

(86) PCT No.: PCT/US2010/059723
§ 371 (c)(1),
(2), (4) Date: Jul. 9, 2012

(87) PCT Pub. No.: WO2011/072144
PCT Pub. Date: Jun. 16, 2011

(65) Prior Publication Data
US 2012/0294386 A1    Nov. 22, 2012

Related U.S. Application Data

(60) Provisional application No. 61/267,965, filed on Dec. 9, 2009, provisional application No. 61/378,629, filed on Aug. 31, 2010.

(51) Int. Cl.
*H04L 27/00* (2006.01)
(52) U.S. Cl.
USPC .......................................................... 375/259
(58) Field of Classification Search
CPC .................. H04B 5/00; H04L 27/00

USPC .......................................................... 375/259
See application file for complete search history.

(56) References Cited

U.S. PATENT DOCUMENTS

| 5,623,518 | A  | * | 4/1997  | Pfiffner ......................... 375/278 |
| 6,301,504 | B1 | * | 10/2001 | Silvian ............................ 607/60 |
| 6,453,200 | B1 |   | 9/2002  | Koslar |
| 6,477,425 | B1 |   | 11/2002 | Nowick et al. |
| 2002/0188333 | A1 |   | 12/2002 | Nowick et al. |
| 2003/0068990 | A1 |   | 4/2003  | Sorrells et al. |
| 2007/0162090 | A1 |   | 7/2007  | Penner |

OTHER PUBLICATIONS

Ghovanloo, "A wideband power-efficient inductive wireless link for implantable microelectronic devices using multiple carriers", IEEE Trans. Circuits Systems I, vol. 54, No. 10, pp. 2211-2221, Oct. 2007.*
Jow, "Modeling and optimization of printed spiral coils in air, saline, and muscle tissue environments", IEEE Trans Biomed Circuits Syst., vol. 3, No. 5, pp. 339-347 Oct. 2009.*
Simard , "High-speed OQPSK and efficient power transfer through inductive link for biomedical implants", IEEE Trans Biomed Circuits Systems, vol. 4, No. 3, pp. 192-200 year 2010.*

(Continued)

*Primary Examiner* — Juan A Torres
(74) *Attorney, Agent, or Firm* — Troutman Sanders LLP; Ryan A. Schneider; Dustin B. Weeks

(57) ABSTRACT

An embodiment provides a pulse harmonic modulation method comprising transmitting a first data initiation pulse to an input of a first resonant circuit thereby creating an oscillating waveform at an output of a second resonant circuit and transmitting a first modifying pulse to the input of the first resonant circuit. The first modifying pulse can modify a first portion of the oscillating waveform.

24 Claims, 19 Drawing Sheets

(56) References Cited

OTHER PUBLICATIONS

Inanlou, "Wideband near-field data transmission using pulse harmonic modulation", IEEE Trans Circuits Syst I, vol. 58, No. 1, pp. 186-195 date Jan. 2011.*

Inanlou, "A 10.2 Mbps Pulse Harmonic Modulation Based Transceiver for Implantable Medical Devices" IEEE Journal of solid-state circuits, vol. 46, No. 6, Jun. 2011.*

Jow, "Design and optimization of printed spiral coils for efficient transcutaneous inductive power transmission", IEEE Trans Biomed Circuits Syst, vol. 1, No. 3, pp. 193-202 year 2007.*

Jow, "Optimization of data coils in a multiband wireless link for neuroprosthetic implantable devices", IEEE Trans. Biomed. Circuits Syst., vol. 4, No. 5, pp. 301-310 Oct. 2010.*

Jow, "Modeling and optimization of printed spiral coils in air, saline, and muscle tissue environments", IEEE EMBS pp. 6387-6390 Sep. 2, 2009.*

International Search Report and Written Opinion dated Feb. 17, 2011 for related PCT Patent Application No. PCT/US2010/059723.

* cited by examiner

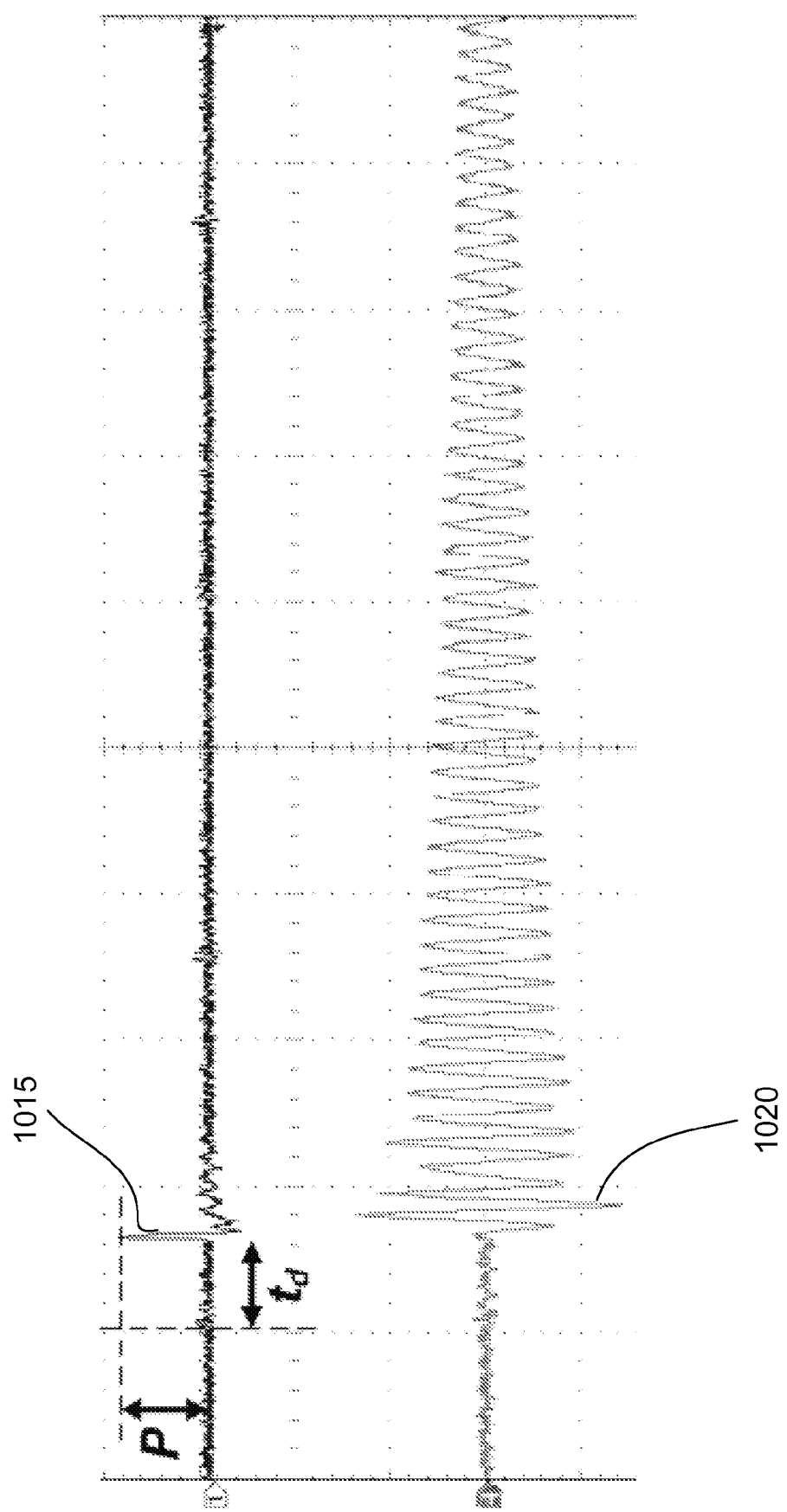

PULSE HARMONIC MODULATION SYSTEMS AND METHODS

CROSS-REFERENCE TO RELATED APPLICATIONS

This application claims the benefit of U.S. Provisional Application Ser. No. 61/267,965, filed 9 Dec. 2009, and U.S. Provisional Application Ser. No. 61/378,629, filed 31 Aug. 2010, both of which are incorporated herein by reference in their entireties as if fully set forth below.

STATEMENT REGARDING FEDERALLY SPONSORED RESEARCH

This invention was made with U.S. Government support under Grant No. ECCS-0824199 awarded by the National Science Foundation. The U.S. Government has certain rights in the invention.

TECHNICAL FIELD OF THE INVENTION

The various embodiments of the present disclosure relate generally to modulation systems and methods. More particularly, the various embodiments of the present invention are directed to pulse harmonic modulation systems and methods.

BACKGROUND OF THE INVENTION

Near-field inductive links have been extensively used in conventional methods for short-range data and power transmission. An inductive link between two magnetically-coupled coils is now one of the most common methods to wirelessly send power and data from the external world to an Implantable Medical Device ("IMD") that requires relatively high data transmission bandwidth. Conventional inductive links include two adjacently coupled LC tank resonant circuits—one on a receiver-side and one on a transmitter side. By tuning these LC tank circuits at a wireless carrier frequency, the amplitude of a transmitted signal on the receiver-side can be increased significantly while attenuating the out-of-bound interference.

There are numerous applications for using inductive links to transmit and receive data. For example, IMDs that can use inductive links to receive data and power include, but are not limited to, neuromuscular stimulators, cochlear implants, visual prostheses, and the like. Further, applications seeking to avoid the use of batteries due to size, cost, and lifetime constraints can highly benefit from inductive coupling systems and methods. Examples of these applications include, but are not limited to, Radio-Frequency Identification ("RFID"), contactless smartcards, wireless Microelectronic Mechanical Systems ("MEMS"), and the like. Achieving high power transmission efficiency, high data transmission bandwidth, and small size while maintaining robustness and a low Bit-Error-Rate ("BER") against impediments, such as external interference, supply ripple, load changes, internal digital switching noise, and coupling variations due to vibrations and coils misalignments, are some of the major challenges in the design of conventional inductive coupling systems.

Some biomedical implants, particularly those that interface with the Central Nervous System ("CNS"), such as cochlear and visual prostheses, need relatively large amounts of data to simultaneously interface with a large number of neurons through multiple channels. In some instances, a minimum of 625-1000 pixels are needed in a visual prosthesis to enable a patient to read text with large fonts. Every stimulation command in such prostheses can require ten bits for addressing the stimulating sites, six to eight bits for stimulation pulse amplitude levels, and two to four bits for polarity, parity-checking, and sequencing. This would suggest at least 20-bits per command frame are required for site selection and stimulus amplitude information. Considering that it might be necessary to stimulate electrodes at rates up to 200 Hz each (for physiological reasons) and there is a need for up to four commands per biphasic-bipolar stimulation pulse in some microstimulator architectures, then raster scanning all 625 sites at this rate requires a serial data bit stream of 625-sites×20-bits×4-commands×200-frames=10 Mbps. The fact that all the electrodes might not need to be refreshed at all times, significantly reduces the required data rate. However, it is clear that a high data transmission bandwidth is needed for wireless implantable microstimulators that interface with the CNS.

Data transmission techniques in conventional systems have mostly been carrier based. In broadband wireless communications, such as the IEEE-802.11a standard for wireless LAN application, data-rates as high as 54 Mbps have been achieved at the expense of increasing the carrier frequency up to 5.8 GHz, which yields a data-rate to carrier-frequency ratio of only 0.93%. In other words, each data bit is carried by 107.4 carrier cycles. Such high carrier frequencies, however, are impractical for use in IMDs. The maximum carrier frequency for biomedical implants is limited to a few tens of MHz (generally 20~30 MHz) due to the coupled coils' self-resonance frequency, increased power loss in the power transmission circuitry at higher carrier frequencies, and excessive power dissipation in the tissue, which increases as the carrier frequency squared ($f_r^2$). Therefore, a goal of conventional inductive coupling systems and methods is to transmit/receive each data bit with a minimum number of carrier cycles in order to maximize the data-rate to carrier-frequency ratio and minimize power consumption.

Implantable devices that record the neural activity and send the information out of the body also need wide bandwidth data links. This is because neural signals have a wide bandwidth (0.1 Hz~10 kHz) and recording from a large number of electrodes generates a large volume of data. Conventional systems have employed different modulation schemes for transmitting data outside the body. A goal of these systems is to use modulation circuitry that is very low power, capable of handling high data rates, and very small. Also, because power and data are often transmitted simultaneously, the data link must be robust in the presence of the power carrier interference, which can be orders of magnitude larger than the data carrier.

Several modulation schemes have been used in conventional systems for data transmission via an inductive link, including Amplitude Shift Keying ("ASK"), On-Off Keying ("OOK"), Frequency Shift Keying ("FSK"), Phase Shift Keying ("PSK"), and Pulse Position Modulation ("PPM"). ASK has been commonly used in conventional systems and methods because of its simple modulation and demodulation circuitry. This method of modulation represents digital data as variations in the amplitude of a carrier signal. ASK, however, is not robust against coupling variations and faces major limitations for high-bandwidth data transmission. High-bandwidth ASK needs high order filters with sharp cut-off frequencies. This requires large capacitors that cannot be easily integrated in the low-frequency end of RF applications.

A remedy that has been proposed is the so-called suspended carrier modulation or On-Off Keying ("OOK"), which is a simple form of ASK that represents digital data as the presence or absence of a carrier wave. OOK boosts the modulation index up to 100% (turning the carrier on and off) to achieve high data rates with low-order integrated filters at the expense of an average 50% reduction in the carrier power. Even with OOK, however, achieving high data-rates is challenging, and data rates are usually less than 10% of the carrier frequency.

FSK and PSK operate by modulating data in the frequency or phase of a sinusoidal carrier wave, respectfully. A limitation with FSK is that it occupies a relatively wide bandwidth (>5 MHz). PSK has fewer limitations compared to ASK, OOK, and FSK. However, the dependence of all of these methods on a carrier signal results in high power consumption, particularly on the transmitter side of the transmissions system.

For wideband data transmission from IMDs to the outside of the body (referred to as the uplink), most conventional systems have employed active back telemetry circuits, such a Voltage Controlled Oscillators ("VCO"), that utilize similar carrier based modulation techniques in the far-field domain. This has been done despite the fact that the external receiver antenna can be placed in a patch right across the skin. As a result, the RF transmitter is one of the key power consuming blocks in such IMDs. An alternative method used in conventional systems is passive back telemetry using Load Shift Keying ("LSK"), which is abundantly used in RFID tags for data rates up to 0.5 Mbps. LSK is limited because of its requirement for strong coupling between coils, a switch across the IMD power coil, and an ASK receiver outside of the body. Although the switch is relatively simple to implement and consumes little power, the switch entirely shuts off the power transfer to the IMD when it is closed. Hence, a fundamental problem with LSK is reducing the IMD received power by the switching duty cycle, which is not desired in high performance IMDs.

In 2002, the U.S. FCC issued a ruling deregulating the use of Ultra-Wide Band ("UWB") for communications. A variation of UWB, known as Impulse Radio ("IR")-UWB, in which data is transmitted via sub-nanosecond pulses through wideband antennas, soon became popular in conventional systems for short-range low applications, such as Body Area Networks ("BAN"). Conventional IR-UWB systems are able to consume small amounts of power because they are carrierless, which means they do not require any continuously on power-consuming, high-frequency oscillators or frequency stabilization circuitry. These characteristics make IR-UWB look like an attractive choice for the uplink in IMDs. The caveat, however, is that the ordinary IR-UWB, which is intended for far-field interactions in the 3.1~10.6 GHz band, is highly absorbed in water; thus, it cannot penetrate or pass through a tissue volume conductor.

Additionally, in UWB, modulation schemes such as OOK and PPM have been used in conventional systems by coding data in the presence and/or location of the pulses. One of the benefits of UWB is the use of discrete pulses for data transmission instead of continuous carrier signals. This eliminates the use for power consuming components such as oscillators, PLLs, and mixers, and, therefore, contributes to the design of low power and low complexity transmitters. There are, however, problems with using these UWB methods in applications where a power carrier is present. The power carrier interference can dominate the data carrier on the receiver side, such that data recovery becomes nearly impossible.

Several conventional systems have adopted the idea of a carrier-less wireless link from the IR-UWB and applied it to inductive links in the near-field domain. These methods use sharp pulses to transfer data in applications, such as chip stacking, multimedia, and BAN. In most of these methods, to achieve high data rates, the Self Resonance Frequencies ("SRF") of both the Transmitter ("Tx") and Receiver ("Rx") coils are kept quite large to allow the high frequency components of the sharp data carrying pulses to effectively pass through the inductive link and reconstruct the pulse on the Rx side. It can be shown that when a simple Gaussian pulse with the width of passes through an inductive link with LC tank circuits on the Rx and Tx sides, the pulse is differentiated by the inductive coupling between the coils and its fundamental frequency shifts from DC to $f_P = \sqrt{2}/\pi t_{pw}$. As a general rule, the inductive link bandwidth should be kept above $2f_P$ to limit undesired Inter-Symbol Interference ("ISI"). Otherwise, if the inductive link bandwidth is not wide enough, it significantly attenuates the higher harmonic components of the sharp transmitted pulse. This results in ringing on the Rx side that extends well beyond the designated bit period. This will either increase the ISI and BER or lead to data rate reduction—both of which are undesirable.

Maintaining high SRF in 100's of MHz range in implanted coils, which are used in IMDs, is not quite feasible because the coils' dimensions, inductance, an separation are often much larger and their parasitic resistance is much lower than that of the on-chip coils used in chip-to-chip communication. Due to high conductivity of the tissue volume conductor, there is also significantly more parasitic capacitance around the IMD coils that are implanted or attached to the body compared to those operating in the air (BAN). Therefore, many of these conventional methods are inapplicable in IMDs.

A possible solution to the bandwidth limitation is lowering the coils' quality factor, Q, by adding series or parallel resistors to the coils. Unlike coils used in IMDs, on-chip coils inevitably have low Qs due to their high parasitic resistance. Low Q, however, has the undesirable effect of decreasing the range of the inductive link, i.e. the maximum coil separation. This occurs because the amplitude of the received signal decreases and the noise and interference due to lowering the receiver selectivity increases, which, consequently, degrades the Rx Signal-to-Noise Ratio ("SNR").

Therefore, there is a desire for systems and methods that take advantage of the low power and low transmitter-complexity properties of conventional UWB methods as well as interference rejection properties of the conventional resonance based methods. Further, there is a desire for systems and methods that allow coils to maintain their high Q, filter out undesired sources of interference, increase the inductive link voltage gain, and maximize the SNR at the Rx.

BRIEF SUMMARY OF THE INVENTION

The present invention relates to pulse harmonic modulation systems and methods. An exemplary embodiment of the present invention provides a pulse harmonic modulation method. The method comprises transmitting a first data initiation pulse to an input of a first resonant circuit thereby creating an oscillating waveform at an output of a second resonant circuit. The method further comprises transmitting a first modifying pulse to the input of the first resonant circuit, wherein the first modifying pulse reduces the inter-symbol interference at the output of the second resonant circuit by modifying a first portion of the oscillating waveform at the output of the second resonant circuit.

In an exemplary embodiment of the pulse harmonic modulation method, the first modifying pulse has a predetermined first amplitude and first time-delay. In another exemplary embodiment of the pulse harmonic modulation method, transmitting the first modifying pulse dampens or decreases the amplitude of the first portion of the oscillating waveform. In yet another exemplary embodiment of the pulse harmonic modulation method, the transmitting the first modifying pulse maintains or increases the amplitude of the first portion of the oscillating waveform. In still yet another exemplary embodiment, the first resonant circuit and/or the second resonant circuit can be located substantially within the body of a user. In another exemplary embodiment, the first resonant circuit and/or the second resonant circuit can be located substantially outside the body of the user.

Some embodiments of the pulse harmonic modulation method further comprise transmitting a second modifying pulse to the input of the first resonant circuit, wherein the second modifying pulse modifies a second portion of the oscillating waveform at the output of the second resonant circuit. Additionally, some embodiments of the present invention can transmit data from the input of the first resonant circuit to the output of the second resonant circuit at a rate of at least five megabits per second.

In addition to pulse harmonic modulation methods, the present invention relates to pulse harmonic modulation systems. An exemplary embodiment of the present invention provides a pulse harmonic modulation system. The pulse harmonic modulation system can comprise a first resonant circuit in communication with a second resonant circuit, wherein the first resonant circuit is enabled to receive a first data initiation pulse, which causes an oscillating waveform at an output of the second resonant circuit, and the first resonant circuit is enabled to receive a first modifying pulse to reduce inter-symbol interference at the output of the second resonant circuit by modifying a first portion of the oscillating waveform.

In an exemplary embodiment of the pulse harmonic modulation system, the first modifying pulse has a predetermined first amplitude and first time-delay. In another exemplary embodiment of the pulse harmonic modulation system, the first modifying pulse modifies the first portion of the oscillating waveform by dampening or decreasing the amplitude of the first portion of the oscillating waveform. In yet another exemplary embodiment of the pulse harmonic modulation system, the first modifying pulse modifies the first portion of the oscillating waveform by maintaining or increasing the amplitude of the first portion of the oscillating waveform. In still yet another embodiment of the pulse harmonic modulation system, the first resonant circuit and/or the second resonant circuit is located substantially within the body of a user. In another exemplary embodiment, the first resonant circuit and/or the second resonant circuit is located substantially outside the body of a user. In an additional exemplary embodiment of the present invention, the distance between the first resonant circuit and the second resonant circuit is less than about 20 millimeters.

In some embodiments of the pulse harmonic modulation system, the first resonant circuit is enabled to receive a second modifying pulse to modify a second portion of the oscillating waveform. Additionally, some embodiments of the present invention are configured to transmit data from the first resonant circuit to the second resonant circuit at a rate of at least five megabits per second.

These and other aspects of the present invention are described in the Detailed Description below and the accompanying figures. Other aspects and features of embodiments of the present invention will become apparent to those of ordinary skill in the art, upon reviewing the following description of specific, exemplary embodiments of the present invention in concert with the figures. While features of the present invention may be discussed relative to certain embodiments and figures, all embodiments of the present invention can include one or more of the features discussed herein. While one or more embodiments may be discussed as having certain advantageous features, one or more of such features may also be used with the various embodiments of the invention discussed herein. In similar fashion, while exemplary embodiments may be discussed below as system or method embodiments, it is to be understood that such exemplary embodiments can be implemented in various devices, systems, and methods of the present invention.

BRIEF DESCRIPTION OF DRAWINGS

The following Detailed Description of preferred embodiments is better understood when read in conjunction with the appended drawings. For the purposes of illustration, there is shown in the drawings exemplary embodiments. But, the subject matter is not limited to the specific elements and instrumentalities disclosed. In the drawings:

FIG. 10B illustrates an exemplary modifying pulse transmitted to the input of the first resonant circuit causing a modifying oscillating waveform at the output of the second resonant circuit in an exemplary embodiment of the present invention.

DETAILED DESCRIPTION OF THE INVENTION

Figure 1:
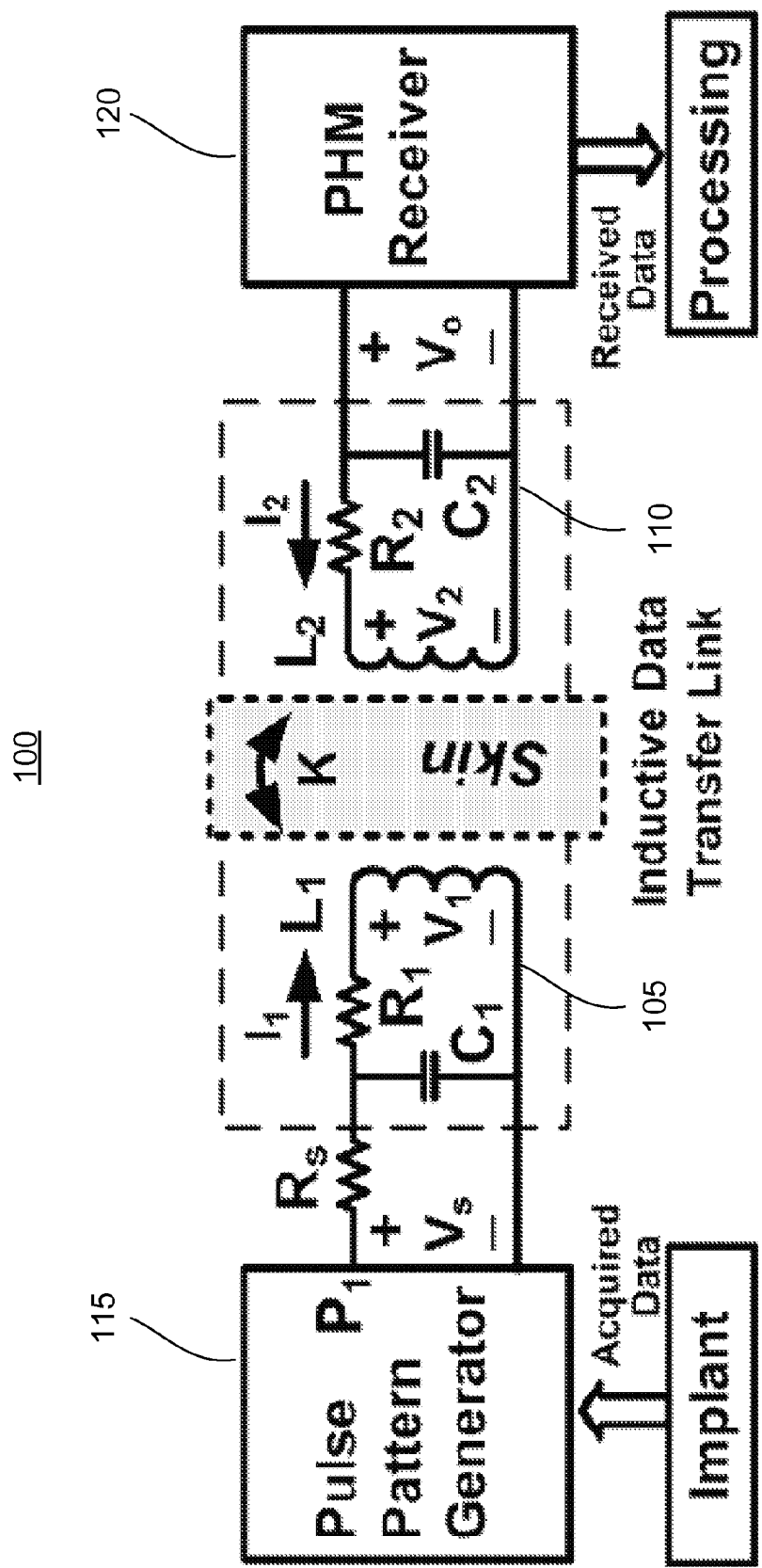
FIG. 1 provides a circuit model schematic of an exemplary embodiment of a pulse harmonic modulation system of the present invention.

To facilitate an understanding of the principles and features of the present invention, various illustrative embodiments are explained below. In particular, the invention is described in the context of being pulse harmonic modulation systems and methods. Embodiments of the present invention may be applied to systems or methods for transmitting data via an inductive link. Embodiments of the invention, however, are not limited to use in systems and methods for transmitting data via an inductive link described herein. As those of ordinary skill in the art would understand, embodiments of the invention can be used by any systems or methods for transmitting data via an inductive link, including, but not limited to, IMD systems, RFID systems, contactless smartcards, MEMS, and the like. Additionally, embodiments of the present invention can be used to transmit data in both near-field and far-field applications.

The components described hereinafter as making up various elements of the invention are intended to be illustrative and not restrictive. Many suitable components or steps that would perform the same or similar functions as the components or steps described herein are intended to be embraced within the scope of the invention. Such other components or steps not described herein can include, but are not limited to, for example, similar components or steps that are developed after development of the invention.

An exemplary embodiment of the present invention provides a pulse harmonic modulation method 1300. The pulse harmonic modulation method 1300 can comprise transmitting a first data initiation pulse to an input of a first resonant circuit thereby creating an oscillating waveform at an output of a second resonant circuit 1305. The method can further comprise transmitting a first modifying pulse to the input of the first resonant circuit, wherein the first modifying pulse reduces the inter-symbol interference at the output of the second resonant circuit by modifying a first portion of the oscillating waveform 1310.

Another exemplary embodiment of the present invention provides a pulse harmonic modulation system 100. The pulse harmonic modulation system 100 can comprise a first resonant circuit 105 in communication with a second resonant circuit 110, wherein the first resonant circuit 105 is enabled to receive a first data initiation pulse, which causes an oscillating waveform at an output of the second resonant circuit 110, and the first resonant circuit 105 is enabled to receive a first modifying pulse to reduce inter-symbol interference at the output of the second resonant circuit 110 by modifying a first portion of the oscillating waveform.

In accordance with an exemplary embodiment of the present invention, the use of narrow pulses for data transmission significantly reduces the consumption of power by the circuitry of a data transmitter. If a narrow pulse is transmitted through an inductive link having resonant circuits tuned to a particular carrier frequency, the inductive link will act as a filter and only let through the main carrier frequency, $f_r$, and a certain bandwidth around it, wherein the bandwidth is dependant on the quality factor, Q, of the resonant circuits. On the receiver side, the pulse causes a sinusoidal oscillating waveform with frequency $f_r$. The oscillating waveform will have a dampening trail due to the natural resistance of the resonant circuit. The rate of damping depends on the Q of the resonant circuits used in the wireless link.

Some of the pulse harmonic modulation systems and methods of the present invention can achieve a high data transmission rate by causing the oscillating waveform caused by a first pulse to dampen very quickly so that the next pulse, which represents the following data bit, can be easily detected. In other words, in order for one data bit, either a "1" or a "0," to be efficiently distinguished from the previous data bit, an exemplary embodiment of the present invention enables the oscillation on the receiver side due to the previous data bit to be dampened significantly before the new data bit is detected. If the oscillating waveform is not dampened quickly enough, Inter-Symbol Interference ("ISI") can result between the oscillations caused by first data pulse and oscillations caused by the second data pulse. If the oscillating waveform dampens too quickly, then an erroneous data value might be detected by the receiver. For example, if the oscillating waveform from a previous pulse dampens too quickly, the receiver may detect a "0" for the current bit period although a "1" was intended. Alternatively, if an oscillating waveform from a previous pulse does not dampen quickly enough, the receiver may detect a "1" for the current bit period although a "0" was intended.

A conventional approach to minimizing ISI is to reduce the Q of the resonant circuits. Decreasing Q, however, leads to an undesired reduction in the voltage gain of the wireless link, which, in turn, leads to a lower transmission range. Additionally, a reduction in Q leads to wider wireless link bandwidth, which weakens the natural filtering effect of the narrow-band link and degrades the SNR of the received signal. High specificity of the data link is important for filtering out the power-carrier and other out-of-band sources of interference, which can be several orders of magnitude larger than the data-carrier on the receiver side. Therefore, there is a desire for systems and methods to be capable of quickly dampening oscillations caused by a data pulse without decreasing the Q of the LC resonant circuits.

FIG. 1 provides an exemplary embodiment of a pulse harmonic modulation system 100. Some embodiments of the pulse harmonic modulation system comprise a first resonant circuit 105 and a second resonant circuit 110. The resonant circuits can be any resonant circuits known in the art. In an exemplary embodiment, each resonant circuit comprises an inductor and its internal parasitic resistor, which are connected in series, connected in parallel to a capacitor. In other embodiments, additional resistors might be added in series with the inductor or in parallel with the capacitor to reduce Q. Some embodiments of the pulse harmonic modulation system 100 further comprise a pulse pattern generator 115 in communication with the first resonant circuit 105 and a receiver 120 in communication with the second resonant circuit 110. The pulse pattern generator 115 can transmit a sequence of pulses to the input of the first resonant circuit 105, which results in an oscillating waveform at the output of the second resonant circuit 110. Some of the pulses can be indicative of data bits. The receiver 120 can detect the pattern of the oscillating waveform to determine the intended data bit values transmitted by the pulse pattern generator 115. To ensure that ISI is minimal at the output of the second resonant circuit 110, the oscillating waveform can be continually modified with modifying pulses so that the receiver 120 can correctly detect the intended data bit values that are transmitted.

Figure 13:
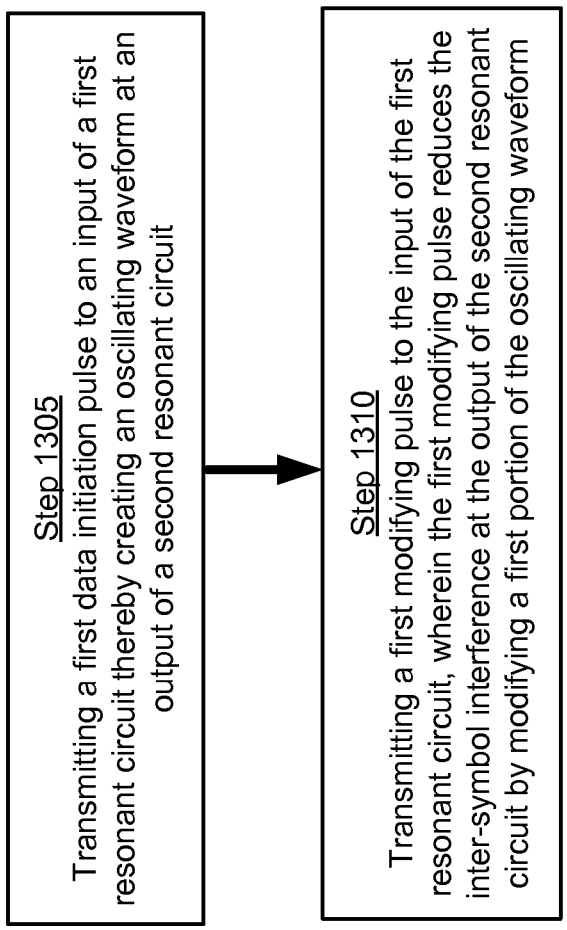
FIG. 13 provides an exemplary embodiment of a pulse harmonic modulation method.

To address the problems with conventional systems, some embodiments of the present invention provide a pulse harmonic modulation method 1300. FIG. 13 provides a flowchart of an exemplary pulse harmonic modulation method 1300 of the present invention. The pulse harmonic modulation method 1300 comprises: transmitting a first data initiation pulse to an input of a first resonant circuit 105 thereby creating an oscillating waveform at an output of a second resonant circuit 110 1305; and transmitting a first modifying pulse to the input of the first resonant circuit 105, wherein the first modifying pulse reduces ISI at the output of the second resonant circuit 110 by modifying a first portion of the oscillating waveform 1310. The pulse harmonic modulation method 1300 can further comprise transmitting additional modifying pulses to the input of the first resonant circuit 105, wherein the additional modifying pulses modify additional portions of the oscillating waveform at the output of the second resonant circuit 110.

In some embodiments of the pulse harmonic modulation method 1300, the modifying pulses enable the oscillation pattern in the oscillating waveform to be modified, such that a receiver can more accurately detect the value of the data bits being transferred by the data initiation pulse. In some embodiments of the present invention, the desired modification of the oscillating waveform can be obtained by transmitting modifying pulses with predetermined amplitudes and time-delays. For example, in order to transmit a data bit with a value of "1," a combination of narrow pulses can be transmitted to the input of the first resonant circuit. The first pulse in the combination of pulses can be a data initiation pulse, which creates an oscillating waveform on the output of the second resonant circuit. After at least one cycle, but during the same bit period, a modifying pulse can be transmitted that continues the oscillating waveform if the following data bit to be transmitted is a "1." Alternatively, a modifying pulse can be transmitted that dampens the oscillating waveform if the following data bit to be transmitted is a "0." In some embodiments of the pulse harmonic modulation method 1300, the step of transmitting the first modifying pulse 1310 increases the amplitude of the first portion of the oscillating waveform (reinforcement pulse). In some embodiments of the pulse harmonic modulation method 1300, the step of transmitting the first modifying pulse 1310 decreases the amplitude of the first portion of the oscillating waveform (suppression pulse).

Figure 2:
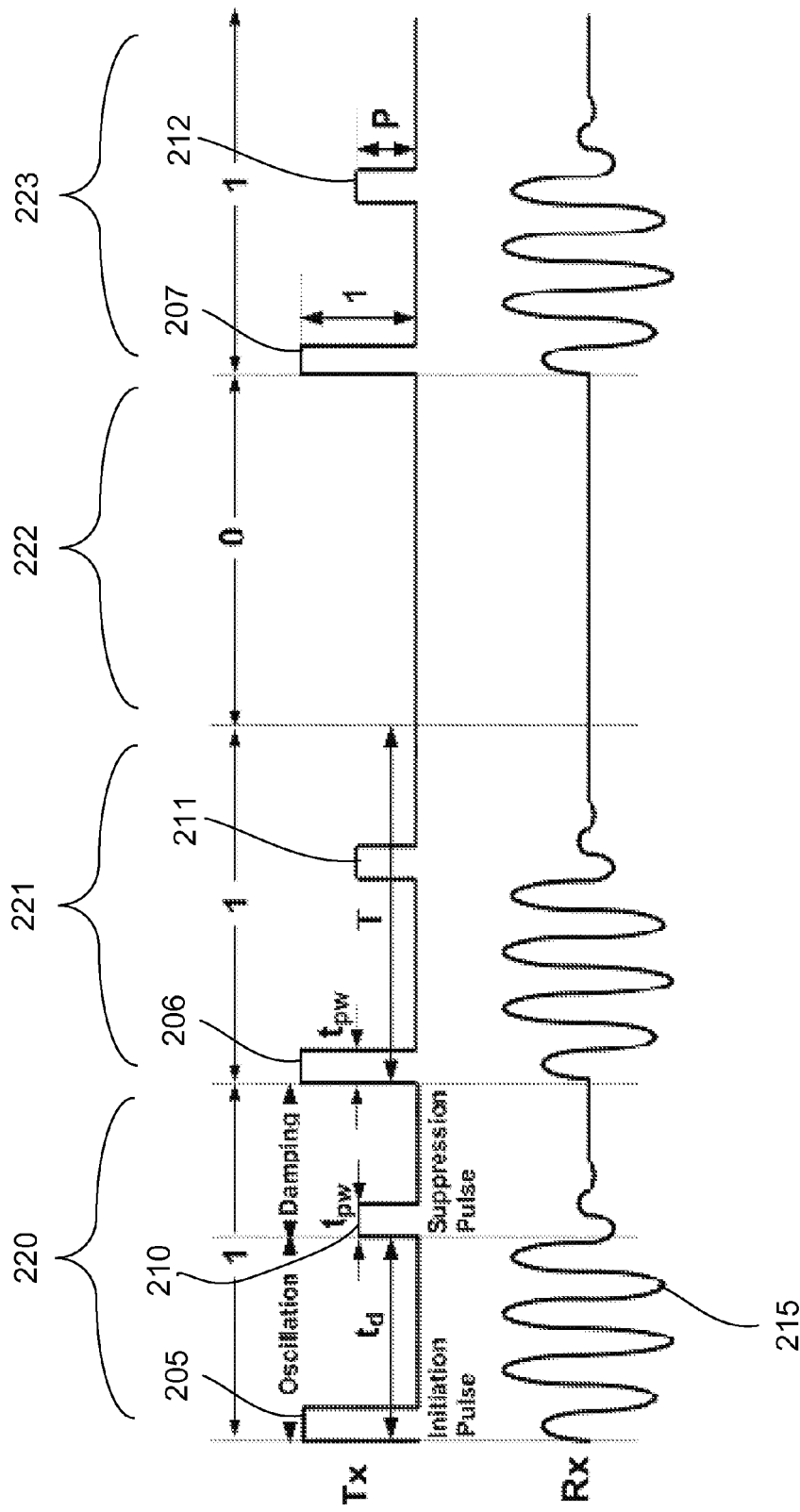
FIG. 2 provides an illustrative waveform example of the effect of a sequence of data initiation pulses and modifying pulses transmitted to the input of a first resonant circuit on an oscillating waveform at the output of a second resonant circuit in an exemplary embodiment of the present invention.

FIG. 2 provides an illustrative example of the effect of a sequence of data initiation pulses and modifying pulses transmitted to the input of a first resonant circuit 105 on an oscillating waveform 215 at the output of a second resonant circuit 110. In the exemplary embodiment, during a first bit period 220, a first data initiation pulse 205 indicative of a data bit with a value of "1" is transmitted to the input of the first resonant circuit 105. The first data initiation pulse 205 causes an oscillating waveform 215 at the output of the second resonant circuit 110. During the first bit period 220 at a predetermined time-delay $t_d$ after the first data initiation pulse 205, a first modifying pulse 210, which has a predetermined amplitude based on an amplitude ratio P, is transmitted to the input of the first resonant circuit 105, which causes the oscillating waveform to dampen in accordance with an exemplary embodiment of the present invention. At the start of the second bit period 221, a second data initiation pulse 206 indicative of a data bit with a value of "1" is transmitted to the input of the first resonant circuit 105. The second data initiation pulse 206 causes an oscillating waveform 215 at the output of the second resonant circuit 110. During the second bit period 221 at a predetermined time-delay $t_d$ after the second data initiation pulse 206, a second modifying pulse 211, which has a predetermined amplitude based on an amplitude ratio P, is transmitted to the input of the first resonant circuit 105, which can cause the oscillating waveform to dampen. During the third bit period 222, no data initiation pulses or modifying pulses are sent to indicate a data bit value of "0." At the start of the fourth bit period 223, a third data initiation pulse 207 indicative of a data bit with a value of "1" is transmitted to the input of the first resonant circuit 105. The third data initiation pulse 207 causes an oscillating waveform 215 at the output of the second resonant circuit 110. During the fourth bit period 223 at a predetermined time-delay $t_d$ after the third data initiation pulse 207, a third modifying pulse 212, which has a predetermined amplitude based on an amplitude ratio "P", is transmitted to the input of the first resonant circuit 105, which can cause the oscillating waveform to dampen. In an exemplary embodiment of the present invention, the sequence of data initiation pulses 205, 206, and 207 and modifying pulses 210, 211, and 212 transmitted to the input of the first resonant circuit can result in a final oscillating waveform 215 at the output of the second resonant circuit 110 indicative of the data sequence "1101."

For each bit period with an intended data bit value of "1," the exemplary embodiment in FIG. 2 follows each data initiation pulse 205, 206, or 207 with a single modifying pulse 210, 211, or 212 during a specific bit period. Other embodiments of the present invention, however, can follow each data initiation pulse with multiple modifying pulses during each bit period. In some embodiments, the use of multiple modifying pulses during each bit period can result in the minimization of ISI and the facilitation of robust data demodulation with low Bit-Error Rate ("BER").

In an exemplary embodiment of the present invention, if a sharp pulse is applied to the input of the first resonant circuit 105, $V_S$, a lowpass filtered version of that pulse can pass as current $I_1$ through a resistor $R_1$ and an inductor $L_1$ of the first resonant circuit 105. The loose mutual coupling, M, between $L_1$ and $L_2$, represented by a small coupling coefficient, $k=M/\sqrt{L_1 L_2}$, can induce a similar but much smaller current, $I_2$, in the inductor $L_2$ of the second resonant circuit, which creates $V_O$ across the output of the second resonant circuit $V_O$ can have an oscillatory nature at a frequency close to the secondary resonance, $f_r = 1/2\pi\sqrt{L_2 C_2}$, and decays exponentially. In some embodiments of the present invention, the amplitude of the $V_O$ oscillations (envelope) drops below 4% of its initial value after $Q_2$ cycles where $Q_2$ is the quality factor of the second resonant circuit 110, $$Q_2 = \frac{1}{R_2}\sqrt{\frac{L_2}{C_2}} \qquad \text{Equation 1}$$

In some embodiments of the present invention, the presence or absence of a pulse at the beginning of every bit period (t=0) represents a data bit "1" or "0," respectively. In some embodiments, the envelope of the $V_O$ oscillating waveform can be negligible at t=T in order to minimize ISI. Therefore, in some embodiments, to achieve a high data rate, the $V_O$ oscillating waveform can decay rapidly, and any residual oscillations beyond t=T can be minimized. This is why conventional systems employed wideband low-Q approaches. These conventional systems are only able to achieve high data rates at the expense of degrading the SNR and selectivity of the receiver 120, which are not acceptable in safe IMD communications.

In contrast to reducing $Q_2$ as in some conventional systems, some embodiments of the pulse harmonic modulation systems and methods modify (modulate) the oscillating waveform pattern of $V_O$, which comprises harmonic components of the data initiation pulse, by transmitting one or more modifying pulses within the same bit period to rapidly suppress the oscillating waveform at $V_O$ before t=T. In the exemplary embodiment shown in FIG. 2, only one modifying pulse with a width, $t_{pw}$, is transmitted in every "1" data bit. P and $t_d$ for the modifying pulse can be selected so that the modifying pulse creates a decaying oscillatory pattern across $V_O$ that is substantially equal and out of phase compared to that of the data initiation pulse from t=$t_d$ to the end of the bit period t=T. P and $t_d$ are dependent on $f_r$, $Q_2$, $t_{pw}$, T, and N, which can be the desired number of cycles at the output of the second resonant circuit 110 for a reliable, low-BER data detection before the oscillating waveform is suppressed. Even though the coupling coefficient, k, may change due to misalignments or mechanical vibrations at a rate much slower than 1/T in some embodiments, because the distance affects all pulses within the bit period in substantially the same way, the pulse harmonic modulation systems and methods can be substantially unaffected.

In some embodiments of the present invention, to derive a mathematical expression for the transfer function between the first resonant circuit 105 and second resonant circuit 110, ($V_O/V_s$), which can be necessary to calculate the pulse harmonic modulation parameters, the resistance, $R_s$, of a pulse pattern generator 115 can be included in the first resonant circuit 105. The pulse pattern generator 115 can be considered an ideal voltage pulse generator. In some exemplary embodiments of the invention used for IMD applications, the values of $R_1$ in the first resonant circuit 105 and $R_2$ in the second resonant circuit 110 are small, unlike chip stacking, because data coils can have a small number of turns that can be either planar and embedded in the Printed Circuit Board ("PCB") or wire-wound and embedded in the IMD packaging. Further, unlike power transmission links, because $I_2$ and k are very small in data transfer links, the effect of the second resonant circuit 110 on the first resonant circuit 105 can be safely neglected by an exemplary embodiment of the present invention, which simplifies equations used to compute the pulse harmonic modulation parameters.

In some embodiments, the relationship between the voltages and currents in the first resonant circuit 105 and the second resonant circuit 110 can be shown by, $$V_1 = L_1 \frac{dI_1}{dt} + M \frac{dI_2}{dt}, V_2 = L_2 \frac{dI_2}{dt} + M \frac{dI_1}{dt} \quad \text{Equation 2}$$

In some embodiments, in order to convert the exemplary embodiment illustrated in FIG. 1 to a pair of parallel resonant circuits, the series $R_1$ and $R_2$ resistors can be changed to their parallel equivalents $R_{1p}$ and $R_{2p}$ using, $$R_{1p}=R_1(Q_1^2+1), R_{2p}=R_2(Q_2^2+1) \quad \text{Equation 3:}$$

where $Q_1$ and $Q_2$ can be calculated using Equation 1. Additionally, in some embodiments, the Thevenin combination of the pulse patter generator 115 voltage source and $R_s$ can be converted to their Norton equivalent, and $R_{1ps}=R_s\|R_{1p}$ can be considered the parallel resistance in the first resonant circuit 105. After simplification, the following transfer function can be obtained:

$$\frac{V_0}{V_S} = \frac{MS}{(R_S L_1 C_1 S^2 + (R_S R_1 C_1 + L_1)S + R_S + R_1)} \quad \text{Equation 4}$$
$$(C_2 L_2 S^2 + C_2 R_2 S + 1)$$

The significance of Equation 4 is that by applying an inverse Laplace transform, the wireless link impulse response can be obtained. Also, the first and second parentheses in the denominator of Equation 4 can be related to the first resonant circuit 105 and second resonant circuit 110, respectively, while the numerator can be related to the coils inductive coupling. In some embodiments, once the parametric values are plugged in to Equation 4, the terms can be separated and the transfer function can be rewritten as, $$H(S) = \frac{V_0}{V_S} = MS\left(\frac{A}{(S+a_1)^2+a_2} + \frac{B}{(S+b_1)^2+b_2}\right) \quad \text{Equation 5}$$

where A, $a_1$, $a_2$, B, $b_1$, and $b_2$ can be functions of the resonant circuits' components. Considering that the numerator in Equation 5 is a differentiation function and the following transformation, $$L^{-1}\left(\frac{a_2}{(S+a_1)^2+a_2}\right) = e^{-a_1 t}\sin(a_2 t) \quad \text{Equation 6}$$

the inductive wireless link impulse response, h(t), can be found in the time domain:

$$h(t) = -\frac{A}{a_2}e^{-a_1 t}[a_1\cos(a_2 t) + a_2\sin(a_2 t)] - \quad \text{Equation 7}$$
$$\frac{B}{b_2}e^{-b_1 t}[b_1\cos(b_2 t) + b_2\sin(b_2 t)]$$

In some embodiments, if $f_r=1/2\pi\sqrt{L_2 C_2}=1/2\pi\sqrt{L_1 C_1}=f_p$ is selected, then according to Equation 7, h(t) can be the subtraction of two exponentially decaying oscillations at $a_2 \approx b_2 \approx 2\pi f_r$, one with a long time constant of $1/b_1 \approx 2R_{2ps}C_2$, and the other one with a short time constant of $1/a_1 \approx 2R_{1ps}C_2$. The result can be an oscillating waveform $V_O$ at the output of the second resonant circuit 110.

In some embodiments of the present invention, after an oscillating waveform is built up from a transmitted data initiation pulse, a modifying pulse is transmitted at time t=$t_d$ to cancel out the $V_O$ oscillating waveform. According to Equation 7, in some embodiments, it can take oscillations about five times the first resonant circuit time constant to build up, i.e. $t_b=\sim 5/a_1$. Therefore, in some embodiments, an amplitude ratio P for the modifying pulse should be found, such that, $$h_{env}(t)=Ph_{env}(t-t_d) \text{ for } t_0 \leq t<T \quad \text{Equation 8:}$$

where $t_0=t_b+t_d$ can be the time when the impulse response of the modifying pulse reaches that of the data initiation pulse, and $H_{env}(t)$ can be the envelope of the wireless link time response in Equation 7, $$h_{env}(t) = -\frac{A}{a_2}e^{-a_1 t} - \frac{B}{b_2}e^{-b_1 t} \qquad \text{Equation 9}$$

In some embodiments, the oscillating waveform resulting from the modifying pulse can be out of phase with respect to oscillating waveform caused by the data initiation pulse. In some of these embodiments, the time delay $t_d$ can be an integer plus a half a cycle, $$t_d = \left(N + \frac{1}{2}\right) \times \frac{1}{f_p} t_b f_r \le N < T f_r \qquad \text{Equation 10}$$

In some embodiments, the predetermined time delay, $t_d$, can be calculated by, $$t_d = \left(N + \frac{1}{2}\right) \times \frac{1}{F_0} 1 \le N < \frac{F_0}{BRF}, \qquad \text{Equation 11}$$

where $F_0$ can be the resonance frequency of the second resonant circuit 110 or the resonance frequency of both first 105 and second 110 resonant circuits, BRF can be the data rate, and N can be the number of oscillations at the output of the second resonant circuit 110 before the oscillating waveform is modified.

In some embodiments of the pulse harmonic modulation systems and methods, the choice of N can not only depend on the oscillation build up time $(4/a_1)$ and the data rate $(1/T)$ on the lower and upper ends, respectively, but it also can depend on the receiver 120 bandwidth and other specifications. A larger value of N can allow more time before the oscillating waveform is modified and can make it easier for the receiver 120 to detect data bits at the cost of slowing down the data rate. A smaller value of N, however, can allow for achieving wider bandwidth and higher data rates.

Even though some of these equations have been based on an ideal impulse response, an advantage of embodiments of the present invention is that as long as the transmitted data initiation pulses and modifying pulses are sharp enough, i.e. $f_p = \sqrt{2}/\pi t_{pw} = f_r$, the systems and methods of the present invention can be applicable by convolving h(t) with any pulse waveform. A sharp square pulse, for example, may not change the shape of h(t).

Figure 3A:
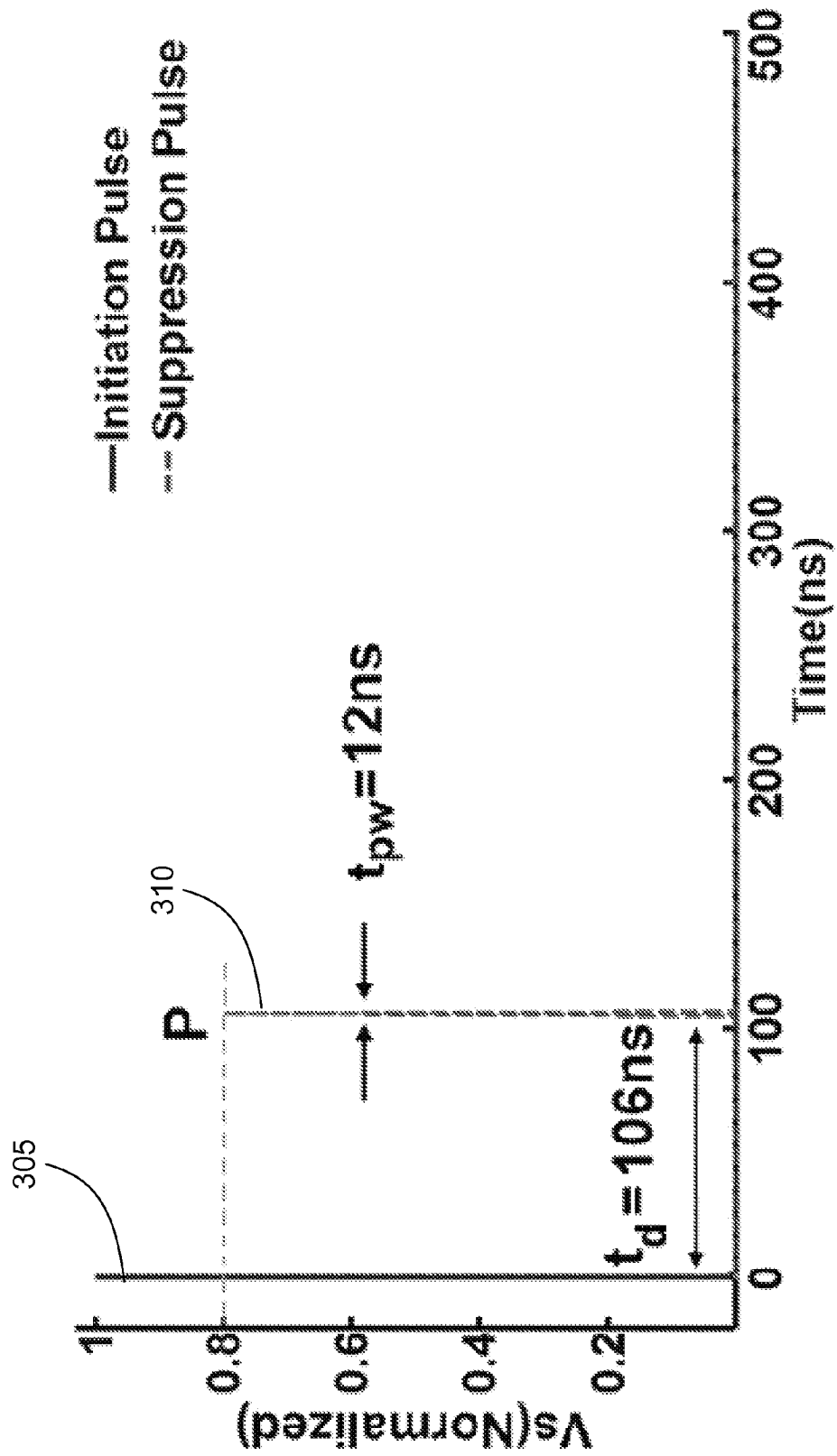
FIG. 3A illustrates a data initiation pulse and modifying pulse (also referred to as suppression pulse) transmitted to the input of a first resonant circuit, which are $t_{pw}=12$ ns wide and $t_d=160$ ns apart, in an exemplary embodiment of the present invention.
Figure 3B:
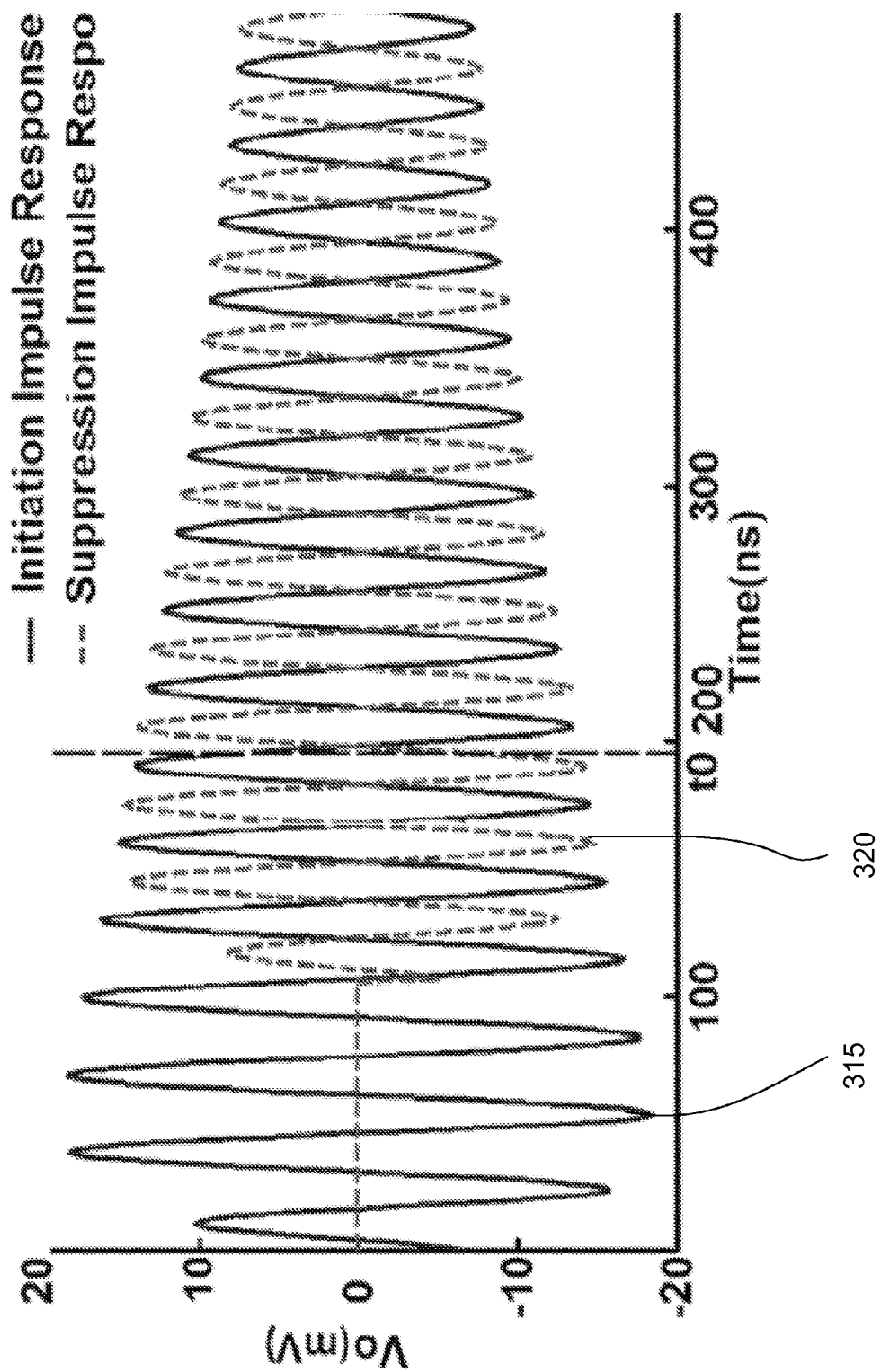
FIG. 3B illustrates a solid oscillating waveform at the output of the second resonant circuit caused by a data initiation pulse and a dashed oscillating waveform caused by a modifying pulse at the output of the second resonant circuit in an exemplary embodiment of the present invention.

FIGS. 3A-3D illustrate data obtained from exemplary embodiments of the present invention. The resonant circuit parameters of the pulse harmonic modulation system 100 embodiment, relied upon to generate the graphs in FIGS. 3A-3D, are provided in Table 1. FIG. 3A illustrates a data initiation pulse 305 and modifying pulse 310 transmitted to the input of a first resonant circuit 105, $V_s$, each of which is $t_{pw}=12$ ns wide. Therefore, the pulse spectral power after differentiation will be centered on $f_p=37.5$ MHz, which is close to the resonance frequency chosen for the inductive link ($f_r=33$ MHz). FIG. 3B illustrates a solid oscillating waveform 315 at the output of the second resonant circuit 110, $V_O$, caused by a data initiation pulse 305 in an exemplary embodiment of the present invention. In an exemplary embodiment, a large $Q_2=41.1$ can result in a slow exponential decay ($2R_{2p}C_2 \approx 390$ ns) in oscillation at the output of the second resonant circuit 110, which can lead to slow data rate or significant ISI if a modifying pulse 320 is not used.

TABLE 1

Exemplary Coils Specifications*

| Coil | Size (cm) | L (nH) | R (mΩ) | $C_p$ (pF) | $C_t$ (pF)** | SRF (MHz) |
|---|---|---|---|---|---|---|
| $L_1$ | 1 × 1 | 105 | 412 | 2.1 | 225 | 338 |
| $L_2$ | 1.9 × 1.9 | 180 | 880 | 4.9 | 132 | 170 |

In the exemplary embodiment illustrated in FIGS. 3A-3D, in order to find the time delay $t_d$, the buildup time for oscillation ($t_b \approx 8R_{1ps}C_1=89.6$ ns when $R_{1ps} R_{s1}=50\Omega$), 1/T for a data rate of 5 Mbps, and $1/f_r=30.3$ ns are all considered. N=3 can be chosen in order to have 3.5 cycles of oscillation at the output of the second resonant circuit 110, $V_O$, before the modifying pulse is transmitted to the input of the first resonant circuit 105. Therefore, in this embodiment, according to Equation 10, $t_d=106$ ns. FIG. 3B provides an illustration of a dashed oscillating waveform 320 at the output of the second resonant circuit 110 by the modifying pulse 310. In an exemplary embodiment, the solid oscillating waveform 315 caused by the data initiation pulse 305 and the dashed oscillating waveform 320 caused by the modifying pulse 310 can be out of phase with each other and reach the same magnitude around $t_0$, which depends on the modifying pulse amplitude ratio, P.

Figure 3C:
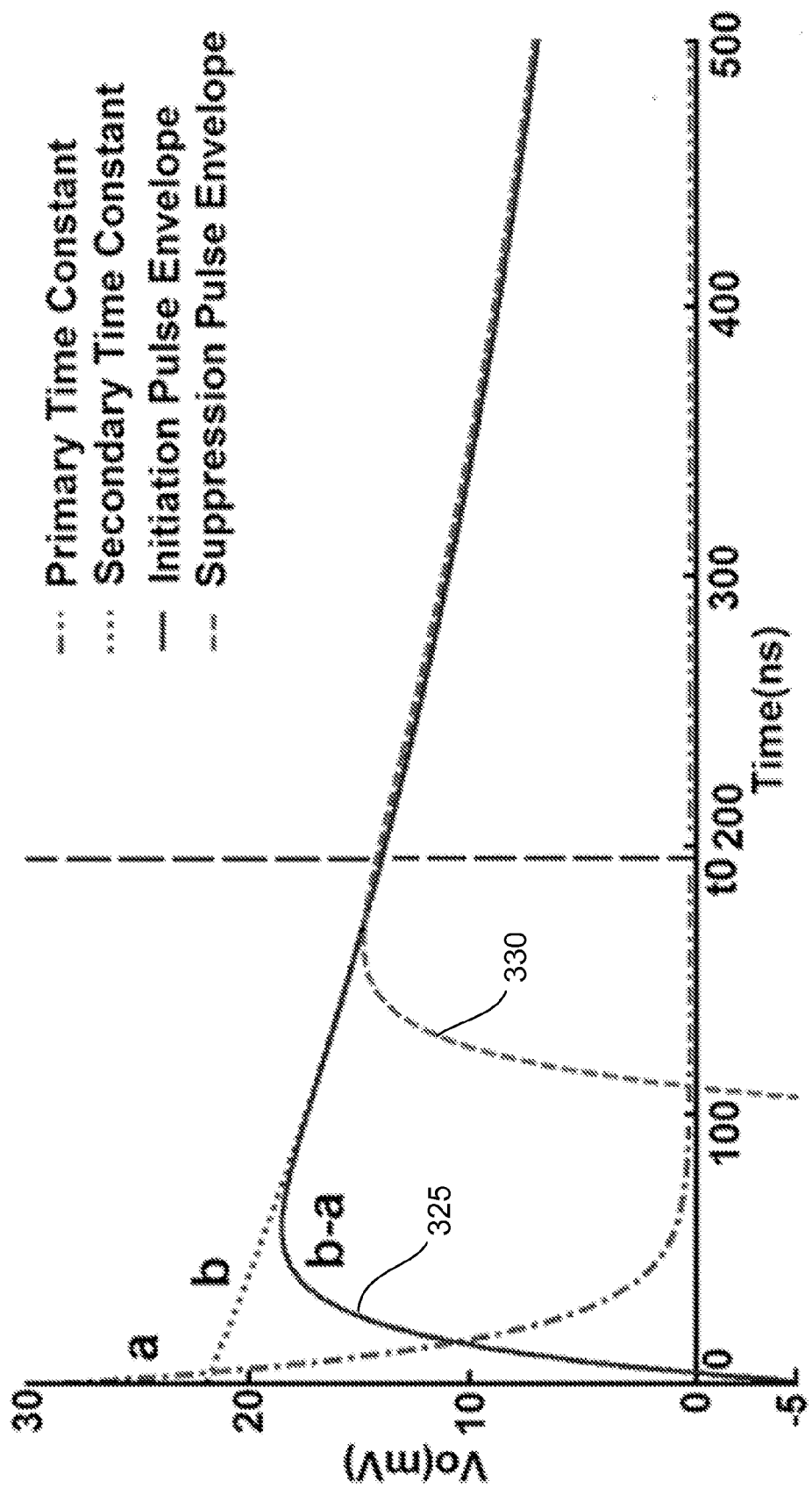
FIG. 3C provides an illustration of the envelope of the solid oscillating waveform, resulting from the data initiation pulse, and the dashed oscillating waveform, resulting from the modifying pulse, in an exemplary embodiment of the present invention.

In some embodiments, if the current data bit is a "1," the amplitude of the modifying pulses is chosen to be one that will effectively cause the oscillating waveform to be suppressed when the following data bit is a "0" and will effectively cause the oscillating waveform to be maintained when the following data bit is a "1." Some embodiments of the present invention find the modifying pulse amplitude ratio, P, by using Equation 9 to consider the envelopes of the received waveforms. FIG. 3C provides an exemplary illustration of the envelope of the solid oscillating waveform 325 and the envelope of the dashed oscillating waveform 330. In the exemplary embodiment shown in FIG. 3C, by plugging in $t_d$ and other parameters from Equation 5 into Equation 8, P=0.8.

Figure 3D:
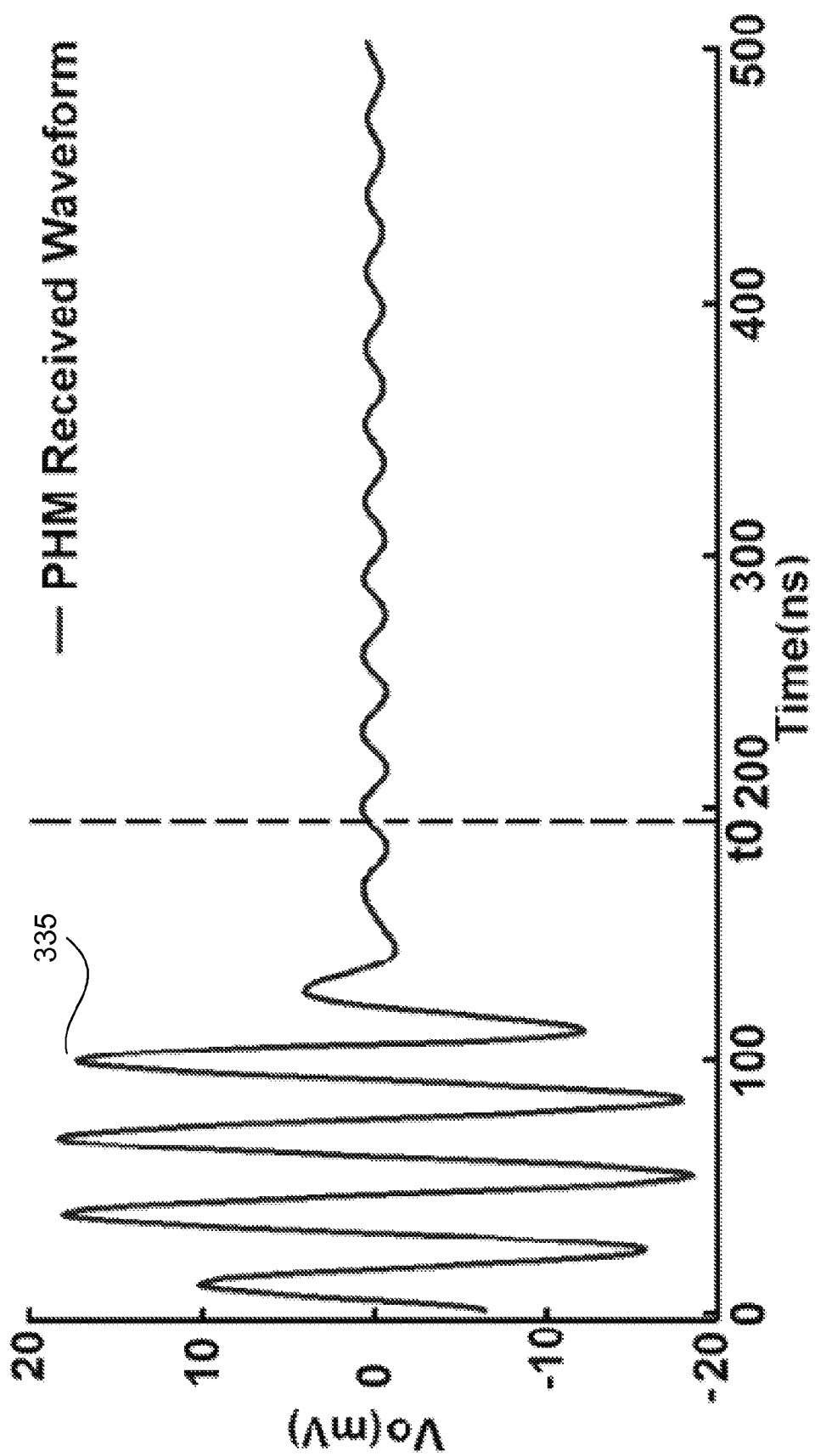
FIG. 3D provides an illustration of a final oscillating waveform at the output of the second resonant circuit in an exemplary embodiment of the present invention.

FIG. 3D provides an exemplary illustration of the final oscillating waveform 335 at the output of the second resonant circuit 110 of an exemplary embodiment of a pulse harmonic modulation system 100 from transmitting the data initiation pulse 305 to the input of the first resonant circuit 105 at time t=0 and transmitting the modifying pulse 310 with a predetermined amplitude, which can be obtained from the amplitude ratio P, and time delay $t_d$ to the input of the first resonant circuit 105 at time t=$t_d$. It can be seen that in this exemplary embodiment the long tail of the solid oscillating waveform 315, which was extending well beyond 500 ns, can be effectively truncated, such that the receiver 120 is ready to detect the following data bit at 1/T=200 ns for a data rate of 5 Mbps with negligible ISI.

Figure 4:
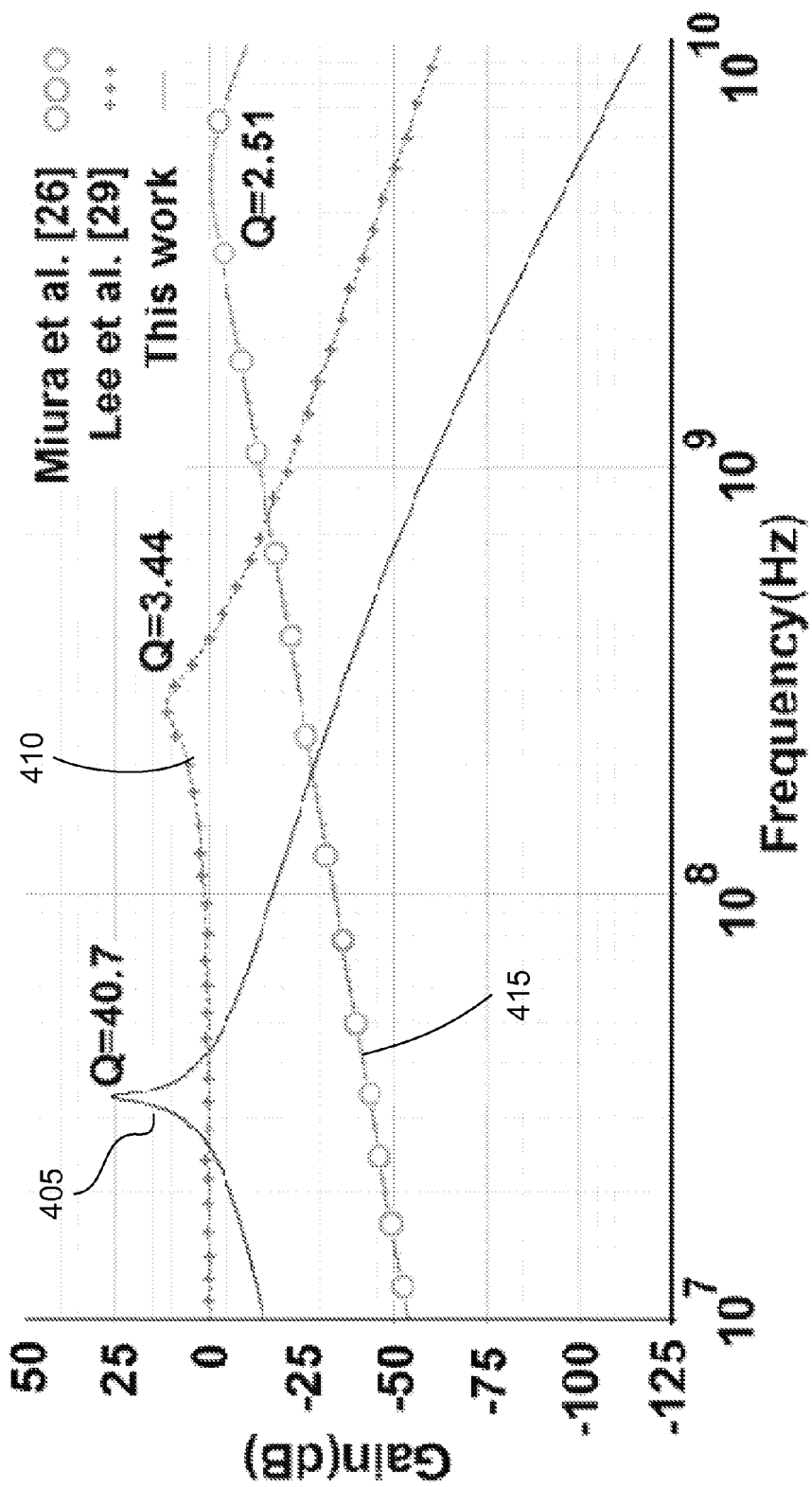
FIG. 4 provides a comparison of the frequency response and quality factor of an exemplary pulse harmonic modulation system of the present invention with the frequency responses and quality factors of conventional systems.

FIG. 4 provides a comparison of the frequency response of an exemplary pulse harmonic modulation system 100 of the present invention 405 with frequency responses of conventional systems 410 and 415. The higher quality factor in the exemplary pulse harmonic modulation system 100, particularly $Q_2$, can result in a higher gain, higher SNR, and better selectivity, which can lead to longer range and more robustness against external interference and coil misalignments, which can be crucial in safe IMD applications.

Figure 5:
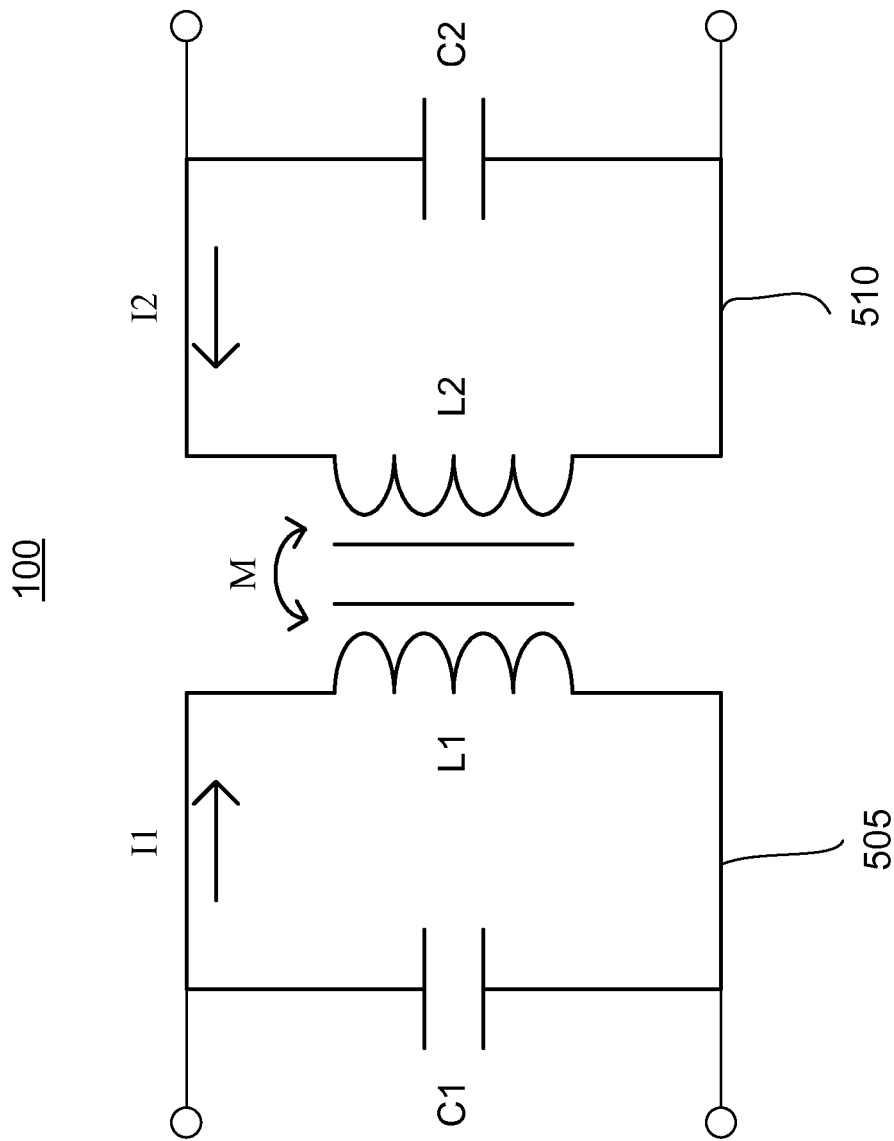
FIG. 5 provides another simplified exemplary embodiment of a pulse harmonic modulation system of the present invention.

FIG. 5 provides another exemplary embodiment of a pulse harmonic modulation system 100. The exemplary pulse harmonic modulation system 100 can comprise a first resonant circuit 505 and a second resonant circuit 510. The first resonant circuit 505 can comprise a first capacitor, $C_1$, connected in parallel with a first inductor, $L_1$. The second resonant circuit 510 can comprise a second capacitor, $C_2$, connected in parallel with a second inductor, $L_2$. The first resonant circuit 505 and the second resonant circuit 510 can be coupled with a coupling coefficient, k, due to their distance from each other. The voltage across the first resonant circuit 505 can be denoted by $V_1$, and the voltage across the second resonant circuit 510 can be denoted by $V_2$. In an exemplary embodiment, $V_1$ and $V_2$ can be represented by, $$V_1 = L_1 \frac{dI_1}{dt} + M \frac{dI_2}{dt}, V_2 = L_2 \frac{dI_2}{dt} + M \frac{dI_1}{dt} \quad \text{Equation 12}$$

The current that passes through the first capacitor can be denoted by $I_1$ and the current that passes through the second capacitor can be denoted by $I_2$. $I_1$ and $I_2$ can be represented by, $$C_1 \frac{dV_1}{dt} = -I_1, C_2 \frac{dV_2}{dt} = -I_2 \quad \text{Equation 13}$$

Equation 12 and Equation 13 can be simplified as, $$\begin{pmatrix} C_1 L_1 & C_1 M \\ C_2 M & C_2 L_2 \end{pmatrix} \begin{pmatrix} I_1 \\ I_2 \end{pmatrix} - \begin{pmatrix} 1 \\ w^2 \end{pmatrix} \begin{pmatrix} I_1 \\ I_2 \end{pmatrix} = 0 \text{ where } \frac{1}{w^2} = \lambda \quad \text{Equation 14}$$

Equation 14 can be simplified as, $$\begin{pmatrix} C_1 L_1 - \lambda & C_1 M \\ C_2 M & C_2 L_2 - \lambda \end{pmatrix} \begin{pmatrix} I_1 \\ I_2 \end{pmatrix} = 0 \quad \text{Equation 15}$$

For Equation 15 to have real roots, the following condition can be met:

$$\begin{vmatrix} C_1 L_1 - \lambda & C_1 M \\ C_2 M & C_2 L_2 - \lambda \end{vmatrix} = 0 \quad \text{Equation 16}$$

Solving Equation 16 and recalling that $$\frac{1}{w^2} = \lambda$$

results in the following:

$$\frac{1}{w^2} = \frac{(C_1 L_1 + C_2 L_2) \pm \sqrt{(C_1 L_1 + C_2 L_2)^2 - 4 C_1 C_2 (L_1 L_2 - M^2)}}{2} \quad \text{Equation 17}$$

Equation 6 defines the resonance frequencies of the first resonant circuit 505 and second resonant circuit 510 for an exemplary embodiment of the present invention. In order to derive the transfer function of the pulse harmonic modulation system 100, basic circuitry theory, such as Kirchhoff's voltage and current laws, can be used. To simplify these calculations, a voltage source with a series resistance, $R_S$, in parallel with the first capacitor, $C_1$, can be added. In some embodiments of the present invention, the transfer function of the pulse harmonic modulation system 100 can then be shown by, $$\frac{V_O}{V_S} = \frac{jwM}{C_1 C_2 R_S (L_1 L_2 - M^2) w^4 - jC2(L_1 L_2 - M^2) w^3 - R_S (L_1 C_1 + L_2 C_2) w^2 + jwL_1 + R_s} \quad \text{Equation 18}$$

In some embodiments of the present invention, parasitic series resistances of $L_1$ and $L_2$ can be added to the resistance of the first and second resonant circuit, respectively. Although this may lead to a more complicated equation for the transfer function than Equation 18, the overall structure of the transfer function can remain the same.

In some embodiments of the present invention, to obtain the Laplace transform of Equation 18, the factor of jw(S) in the numerator of Equation 18 is not taken into account. However, after calculating the Laplace transform without S, the derivative of the resulting equation in the time domain can be calculated to make up for the S factor in the numerator. In the S domain, such a transfer function can be written in the form of individual first order terms:

$$\frac{1}{(S+a)(S+b)(S+c)(S+d)} = \quad \text{Equation 19}$$

$$\frac{A}{(S+a)} + \frac{B}{(S+b)} + \frac{C}{(S+c)} + \frac{D}{(S+d)}$$

where $a=a_1+ia_2$, $b=b_1+ib_2$, $c=c_1+ic_2$, $d=d_1+id_2$, $a_1=b_1$, $a_2=-b_2$, $c_1=d_1$, and $c_2=-d_2$.

Because $$L^{-1}\left(\frac{A}{(S+a)}\right) = e^{-at},$$

the inverse Laplace transform of Equation 19 in the time domain will be the impulse response h(t), where, $$h(t) = -(A+B)e^{-a_1 t}[a_1 \cos(a_2 t) + a_2 \sin(a_2 t)] - (C+D)e^{-c_1 t} [c_1 \cos(c_2 t) + c_2 \sin(c_2 t)] \quad \text{Equation 20:}$$

The output Out(t) of the pulse harmonic modulation system 100 for the input In(t) can be defined by, $$\text{Out}(t) = \text{In}(t) * h(t) \quad \text{Equation 21:}$$

Calculating the coefficients for the impulse response can involve extensive calculations. Therefore, in some embodiments of the present invention, specialized software, such as MATLAB, can be used to determine the coefficients for the impulse response in Equation 20. Qualitative observations and basic knowledge of resonant circuits can lead to the conclusion that the oscillation coefficients, $a_2$ and $c_2$, are dependent on $L_1$, $C_1$, $L_2$, $C_2$, and M, and the decay coefficients, $a_1$ and $c_1$, are dependent on the parasitic series resistances of $L_1$, $L_2$, and $R_S$.

Figure 6:
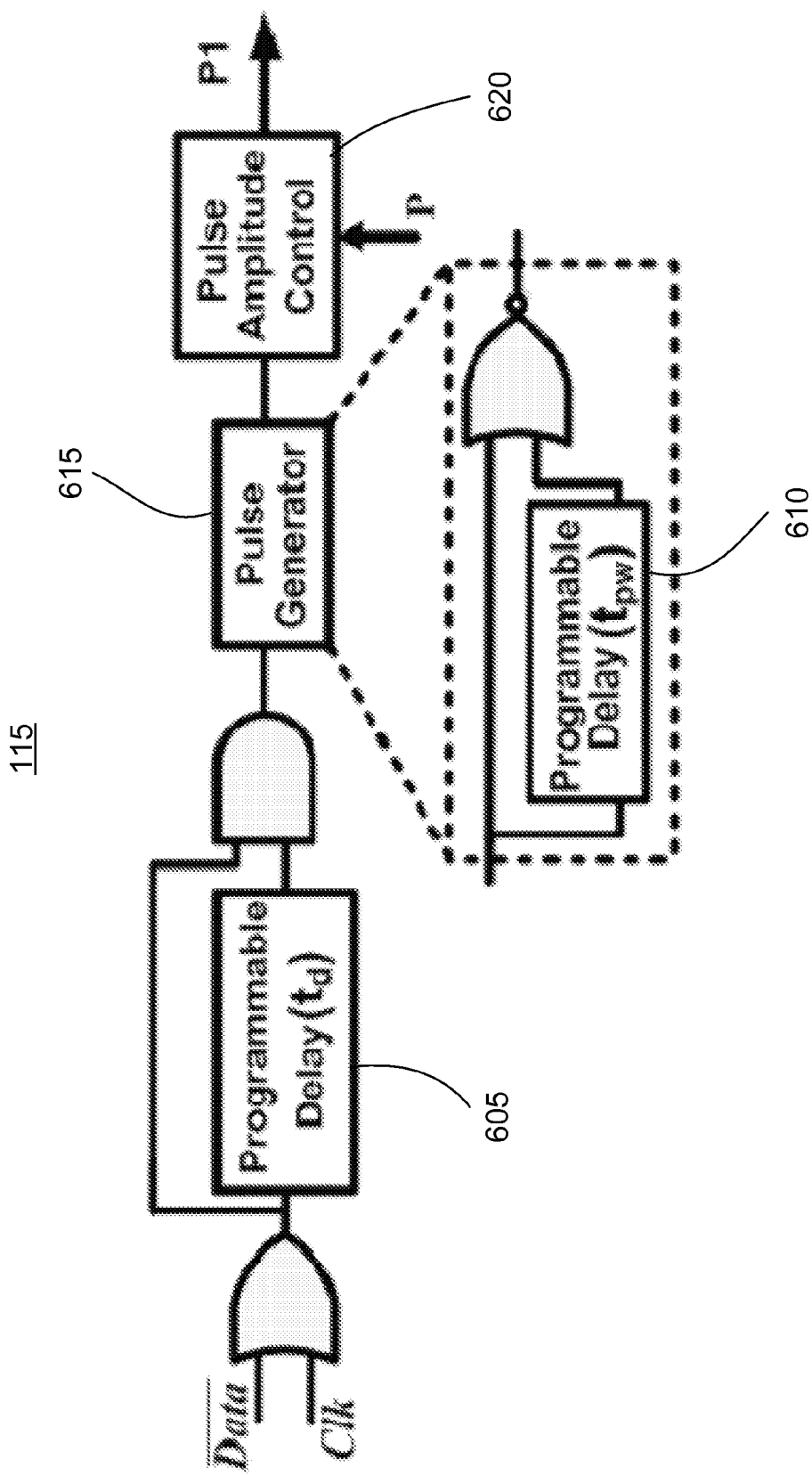
FIG. 6 provides a block diagram of an exemplary pulse patter generator of the present invention.

Some embodiments of the present invention provide a pulse harmonic modulation system 100 comprising a pulse pattern generator 115. FIG. 6 provides a block diagram of an exemplary pulse patter generator 115. An exemplary embodiment of a pulse pattern generator comprises a first programmable delay element 605, a second programmable delay element 610, a pulse generator 615, and a pulse amplitude control block 620. In an exemplary embodiment of the present invention, the pulse pattern generator 115 can be implemented using an Altera Cyclone II Field Programmable Gate Array ("FPGA"). Those skilled in the art, however, would recognize that the pulse pattern generator 115 could be implemented in numerous ways, which should be considered within the scope of this invention. Because data initiation pulses are only generated for "1" data bits in some embodiments, Data+Clk can be used as the input to the pulse pattern generator 115. In some embodiments, the Data+Clk signal goes low only when the data value is "1" and the clock is "0." In some embodiment of the present invention, the first programmable delay element 605 and second programmable delay element 610 can be used to allow control of the time delay $t_d$ and the pulse width $t_{pw}$, respectively, of the data initiation pulses and modifying pulses, respectively. In some embodiments, the time delay of the modifying pulse is the same if the modifying pulse is increasing or decreasing the amplitude of the oscillating waveform because modifying pulses can each have positive or negative polarity. In some other embodiments, the modifying pulses all have the same polarity (positive only or negative only), but the time delay of each modifying pulse can change depending on whether the modifying pulse is increasing or decreasing the amplitude of the oscillating waveform. In an exemplary embodiment, the first programmable delay element 605 and the second programmable delay element 610 comprise a chain of current starved inverters. The pulse generator block 615 can combine the input with its delayed version to produce a sharp pulse. The pulse amplitude control block 620 can be implemented using a simple ladder network or a high speed Digital to Analog Converter ("DAC"). In any case, the modifying pulse amplitude ratio P can be digitally controllable. In some embodiments, the pulse amplitude control block 620 can use a memory cell to determine the desired amplitude for each modifying pulse, such as an EEPROM, in which there can be a table for the amplitude of each pulse based on a certain number of previous bit values. A table of exemplary modifying pulse amplitudes for a given time delay where the previous bit and the current bit are considered is provided in Table 2. Some embodiments of the present invention comprise a table of modifying pulse amplitudes based on two or more previous bits and the current bit. As the data rate increases, considering a greater number of previous bits to predetermine the amplitude for a current modifying pulse can result in lower ISI and increased system robustness.

TABLE 2

Exemplary Modifying Pulse Amplitudes Based on Past and Current Data Bit Values

| Previous Bit | Current Bit | Pulse Amplitude |
|---|---|---|
| 0 | 0 | 0 |
| 0 | 1 | −1 |
| 1 | 0 | 0.8 |
| 1 | 1 | −0.2 |

Figure 7:
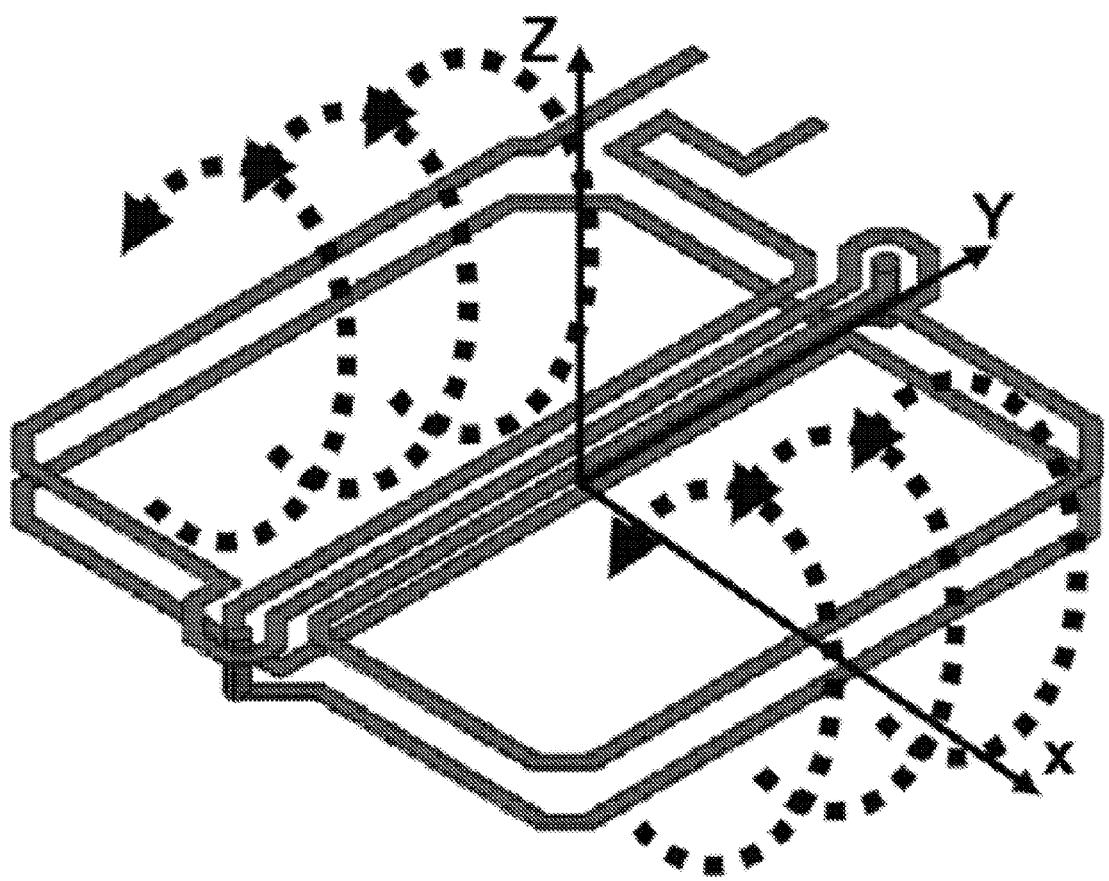
FIG. 7 provides an illustration of an exemplary 3-D model of a figure-8 coil in the HFSS field solver, which can be used in the exemplary resonant circuits of the present invention.
Figure 8:
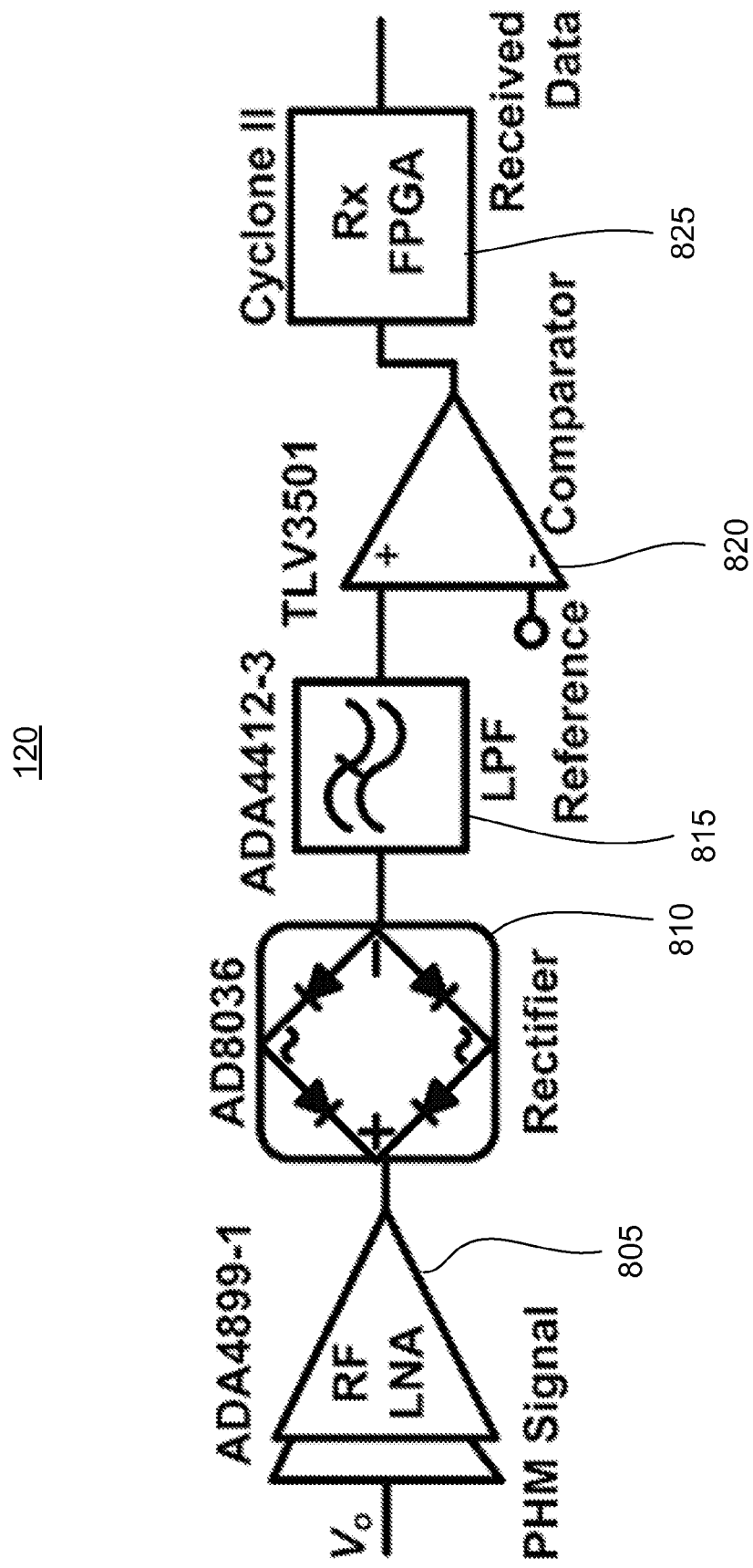
FIG. 8 provides a simplified block diagram of an exemplary receiver of the present invention.

In an exemplary embodiment of the pulse harmonic modulation system 100, in order to construct the first resonant circuit 105 and second resonant circuit 110, figure-8 coils can be used on FR4 PCB substrate. FIG. 7 provides an illustration of an exemplary 3-D model of a figure-8 coil in the HFSS field solver. One reason why the geometry of this exemplary embodiment is advantageous in IMD applications is its resilience against external magnetic field interference, which is key in a multiband transcutaneous inductive wireless link. When a figure-8 coil is exposed to a uniform or symmetrical external magnetic field, the currents induced in the two loops of each coil can cancel out due to their opposing directions of winding, while the two data coils can maintain a decent coupling. Table 1 summarizes the measured specifications of the coils in an exemplary embodiment of the present invention. In an exemplary embodiment, coil geometries can be designed for an uplink with a nominal coil separation of d=10 mm In some embodiments of the present invention, the first resonant circuit 105 and/or the second resonant circuit 110 can be located substantially within the body of a user. In these embodiments, the first resonant circuit 105 and/or the second resonant circuit 110 can be small in size and can be embedded within an IMD. In some embodiments, the first resonant circuit 105 and/or the second resonant circuit 110 can be located substantially outside the body of the user. In an exemplary embodiment of the present invention, when the two resonant circuits are perfectly aligned, they have a simulated k=0.012. $C_p$ can be the coils parasitic capacitance needed for each resonant circuit (including $C_p$) to tune it at $f_r$=33 MHz.

Some embodiments of the pulse harmonic modulation system 100 comprise a receiver 120. FIG. 8 provides a simplified block diagram of an exemplary receiver 120. In an exemplary embodiment of the present invention, the receiver 120 comprises a Low Noise Amplifier ("LNA") 805, a rectifier 810, and a lowpass filter 815. In an exemplary embodiment, the LNA has a gain of 26 dB. In another exemplary embodiment, the lowpass filter 815 has a cutoff frequency of 9 MHz. In some embodiments, a high speed comparator 820 can compare a LPF output, which can be the envelope of the final oscillating waveform 325 with a reference voltage to sharpen the received pulses and convert them to logic levels. In some embodiments, an FPGA board 825 can oversample the received pulses and convert them to a serial data stream. In an exemplary embodiment, the FPGA board is an Altera Cyclone GPGA board. In another exemplary embodiment, the FPGA board 825 oversamples the received pulses at 48 MHz.

Figure 9:
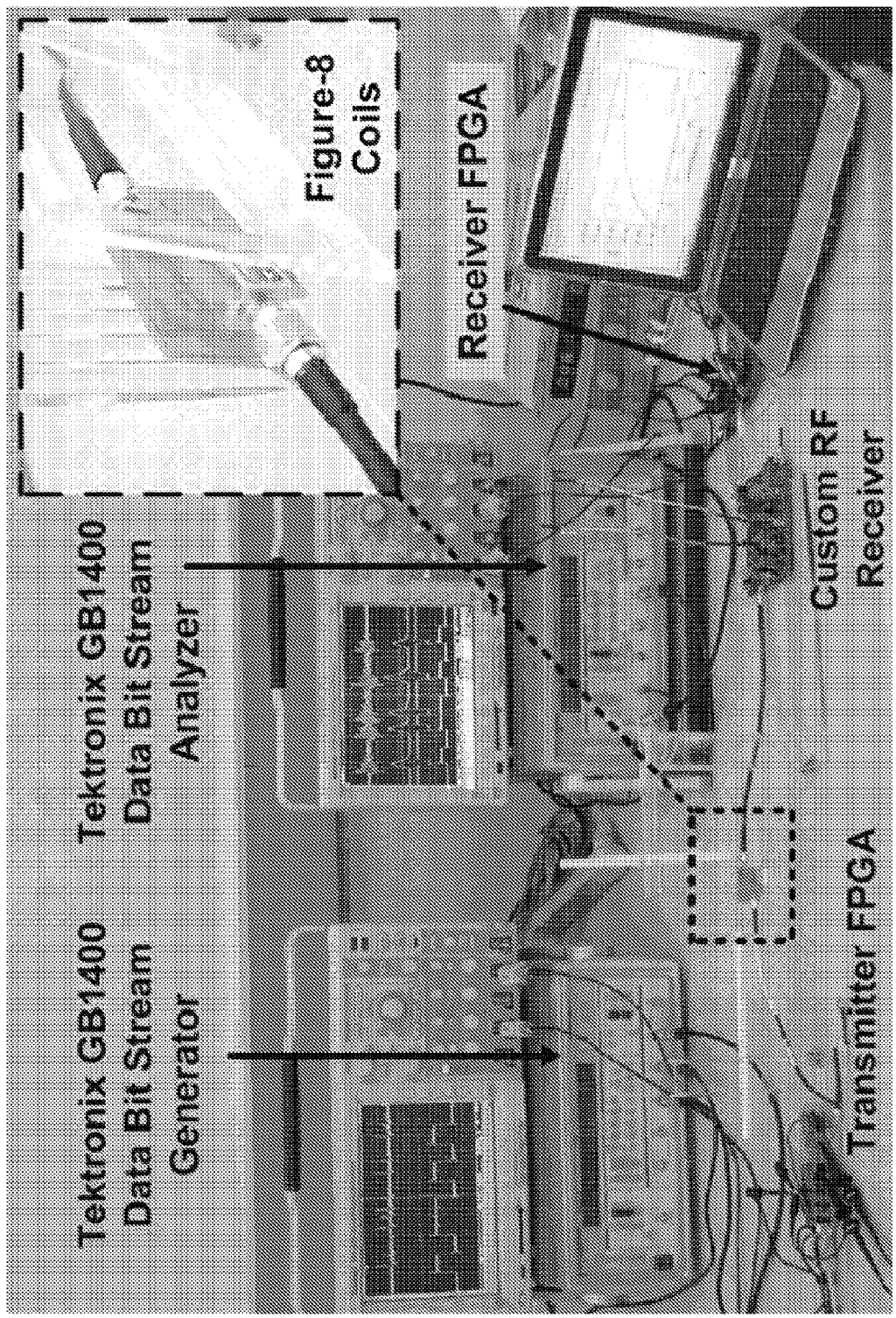
FIG. 9 provides an illustration of a measurement setup to test an exemplary embodiment of the present invention.

FIG. 9 provides an illustration of a measurement setup to test an exemplary embodiment of the present invention. The setup can comprise of Tektronix GB 1400 (GigaBert) on the pulse patter generator 115 side and receiver 120 side, before and after the two FPGA boards, for high speed data bit stream generation and BER analysis, respectively.

Figure 10A:
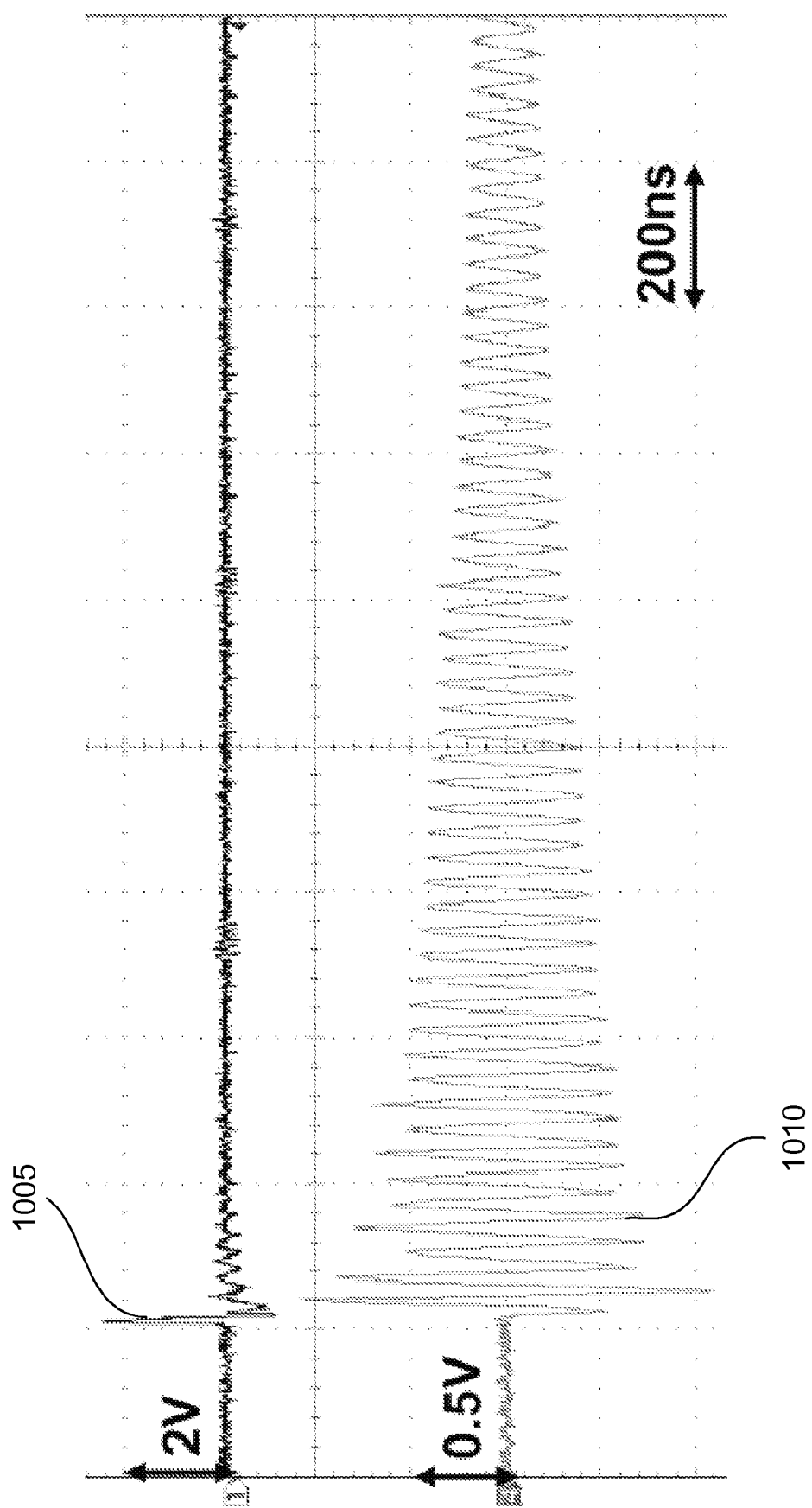
FIG. 10A illustrates an exemplary data initiation pulse transmitted to the input of the first resonant circuit causing a data initiation oscillating waveform at the output of the second resonant circuit in an exemplary embodiment of the present invention.
Figure 10C:
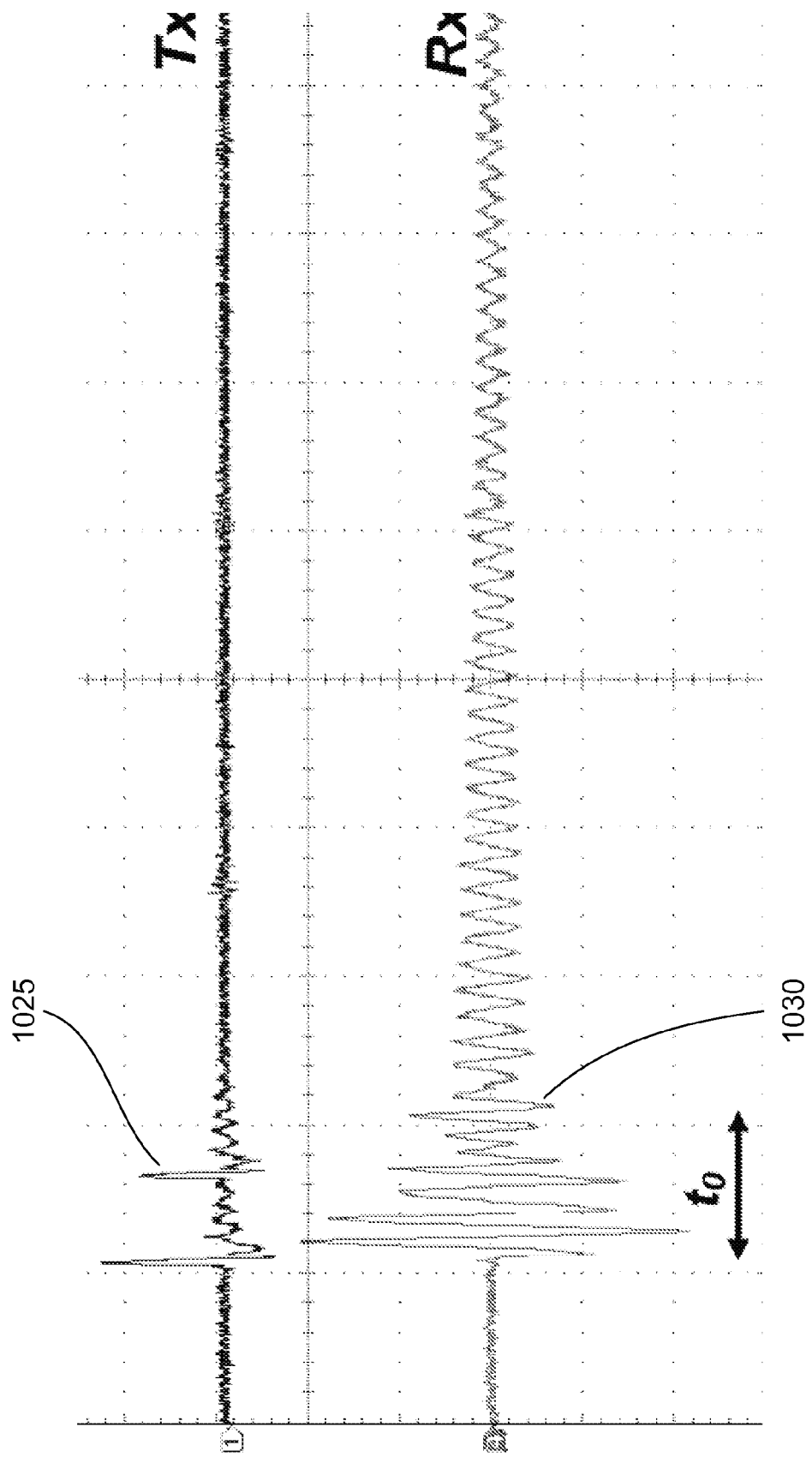
FIG. 10C illustrates an exemplary data initiation pulse followed by a modifying pulse transmitted to the input of the first resonant circuit causing a pulse harmonic modulated oscillating waveform at the output of the second resonant circuit in an exemplary embodiment of the present invention.

FIGS. 10A-10C illustrate measured waveforms at the input to the first resonant circuit 105 and output of the second resonant circuit 110 in an exemplary embodiment of the present invention. FIG. 10A illustrates an exemplary data initiation pulse transmitted to the input of the first resonant circuit 1005 causing a data initiation oscillating waveform at the output of the second resonant circuit 1010. FIG. 10B illustrates an exemplary modifying pulse transmitted to the input of the first resonant circuit 1015 causing a modifying oscillating waveform at the output of the second resonant circuit 1020. It can be seen that a high quality factor has led to slow decay in the data initiation oscillating waveform 1010 and modifying oscillating waveform 1020. This slow decay can lead to high ISI if the data initiation pulse is not followed by a modifying pulse to dampen the oscillating waveform at the output of the second resonant circuit 110. FIG. 10C illustrates an exemplary data initiation pulse followed by a modifying pulse transmitted to the input of the first resonant circuit 1025 causing a pulse harmonic modulated oscillating waveform at the output of the second resonant circuit 1030. The quick dampening in the exemplary pulse harmonic modulated oscillating waveform 1030 results in a significant reduction of ISI, which allows data rates in excess of 5 Mbps. While some embodiments of the systems and methods of the present invention are capable of transmitting data at rates exceeding 5 Mbps, the embodiments can also be applied to applications requiring slower data transmission rates.

Table 3 provides a list of data rates and BER obtained at particular coil sizes and distances with an exemplary embodiment of the present invention (the PHM modulation scheme) and conventional systems.

TABLE 3

CM-Range Inductive Data Telemetry Benchmarking

| Modulation Scheme | Coil Size Tx/Rx (cm) | Distance (cm) | Carrier Freq. (MHz) | Data Rate (Mbps) | BER |
|---|---|---|---|---|---|
| pcFSK | 2/1.2 | 0.5 | 5/10 | 2.5 | $10^{-5}$ |
| BPSK | 3.5/2.7 | 1.5 | 10 | 1.12 | $10^{-5}$ |
| BPSK | N/A | 1~1.5 | 20 | 2 | $10^{-7}$ |
| QPSK | N/A | N/A | 13.56 | 8 | N/A |
| LSK | 3.5/3.5 | 2 | 25 | 2.8 | $10^{-6}$ |
| BPM | 1/1 | 1 | — | 200 | N/A |
| BPM | 1.5/1.5 | ~1 | — | 10 | N/A |
| PHM | 1/1.9 | 1 | (33) | 5.2 | $10^{-6}$ |

Figure 11:
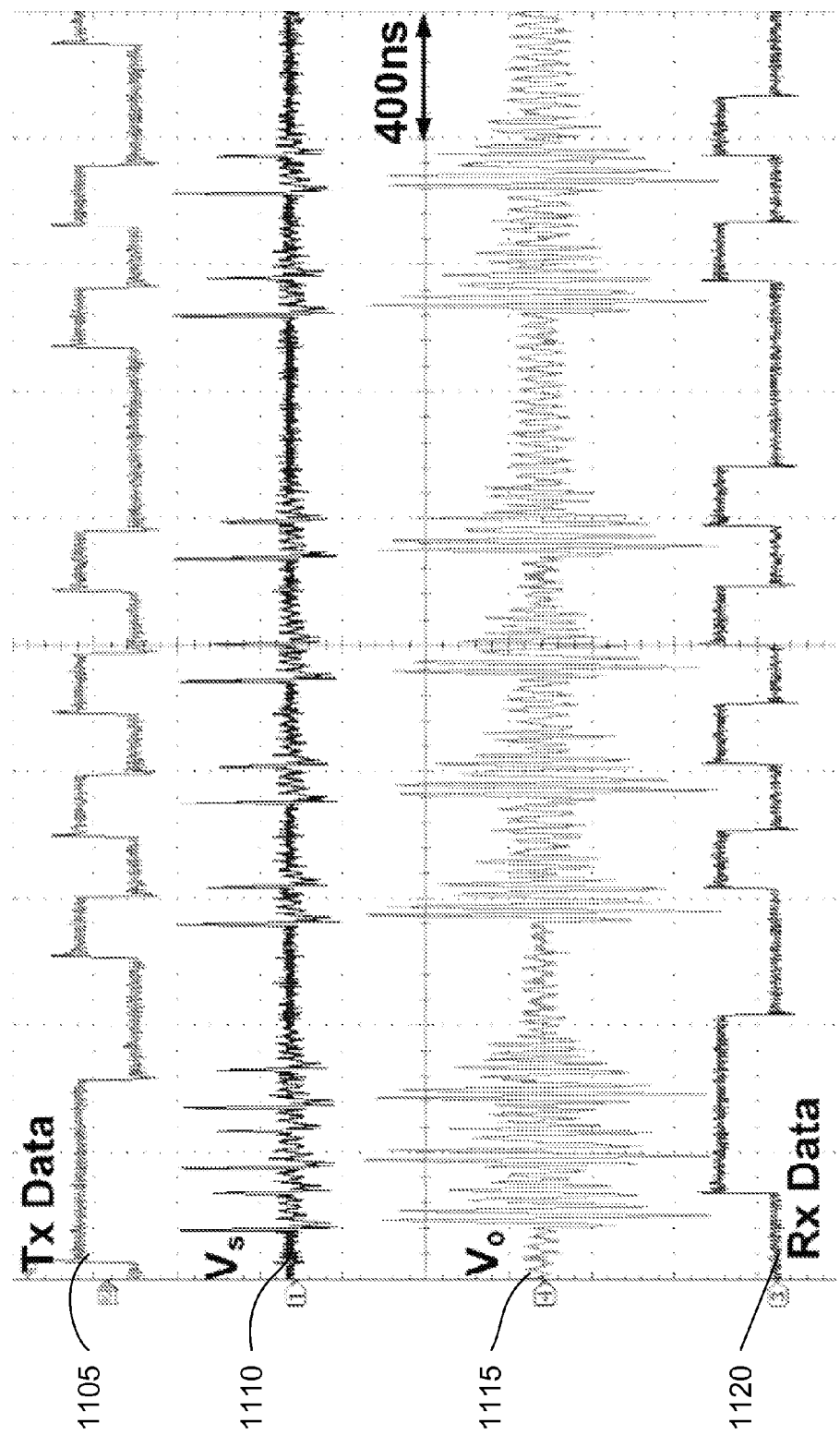
FIG. 11 illustrates measured inputs and outputs using exemplary pulse harmonic modulation systems and methods of the present invention.

FIG. 11 illustrates measured inputs and outputs using exemplary pulse harmonic modulation systems and methods. The intended transmitted data stream 1105 is relayed by transmitting a sequence of data initiation and modifying pulses 1110 to the input of the first resonant circuit 105. The sequence of data initiation and modifying pulses 1110 causes an oscillating waveform 1115 at the output of the second resonant circuit 110. The oscillating waveform 1115 can be processed by the receiver 120 to obtain the received data stream 1120. The exemplary pulse harmonic modulation system 100 measured in FIG. 11 has a data rate of 5.2 Mbps with figure-8 coils aligned at d=1 cm. Those skilled in the art would understand that the distance between the first resonant circuit 105 and the second resonant circuit 110, d, can be any distance. In some embodiments of the invention, d is less than or equal to 2 cm. In other embodiments, however, d can have large values depending on the particular application implementing the systems or methods of the present invention.

Figure 12A:
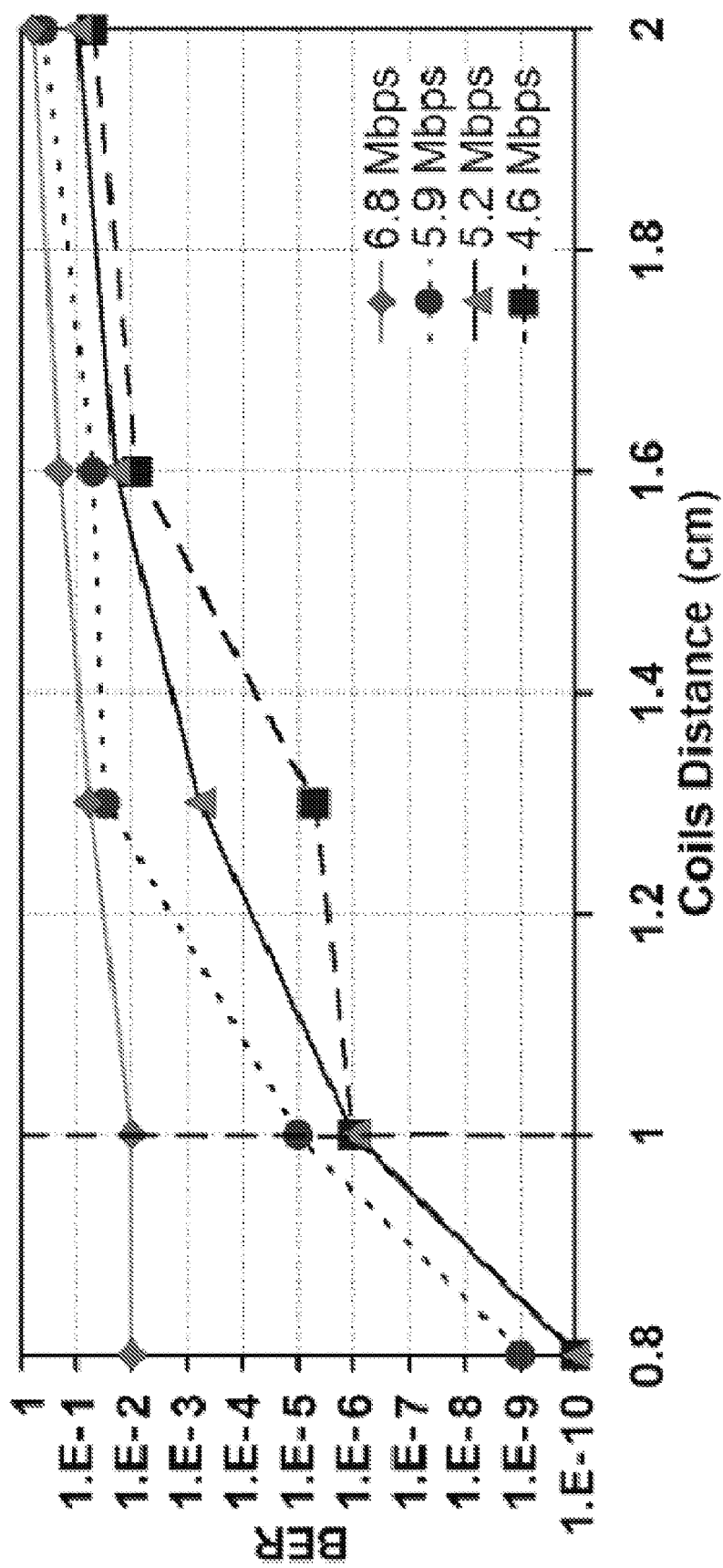
FIG. 12A provides the measured BER at different data rates of exemplary embodiments of the present invention when d is changed from 8 to 20 mm.

FIG. 12A provides the measured BER at different data rates of exemplary embodiments of the present invention when d is changed from 8 to 20 mm This exemplary embodiment of the present invention can achieve a data rate of 5.2 Mbps when d=1 cm with a BER of $10^{-6}$.

Figure 12B:
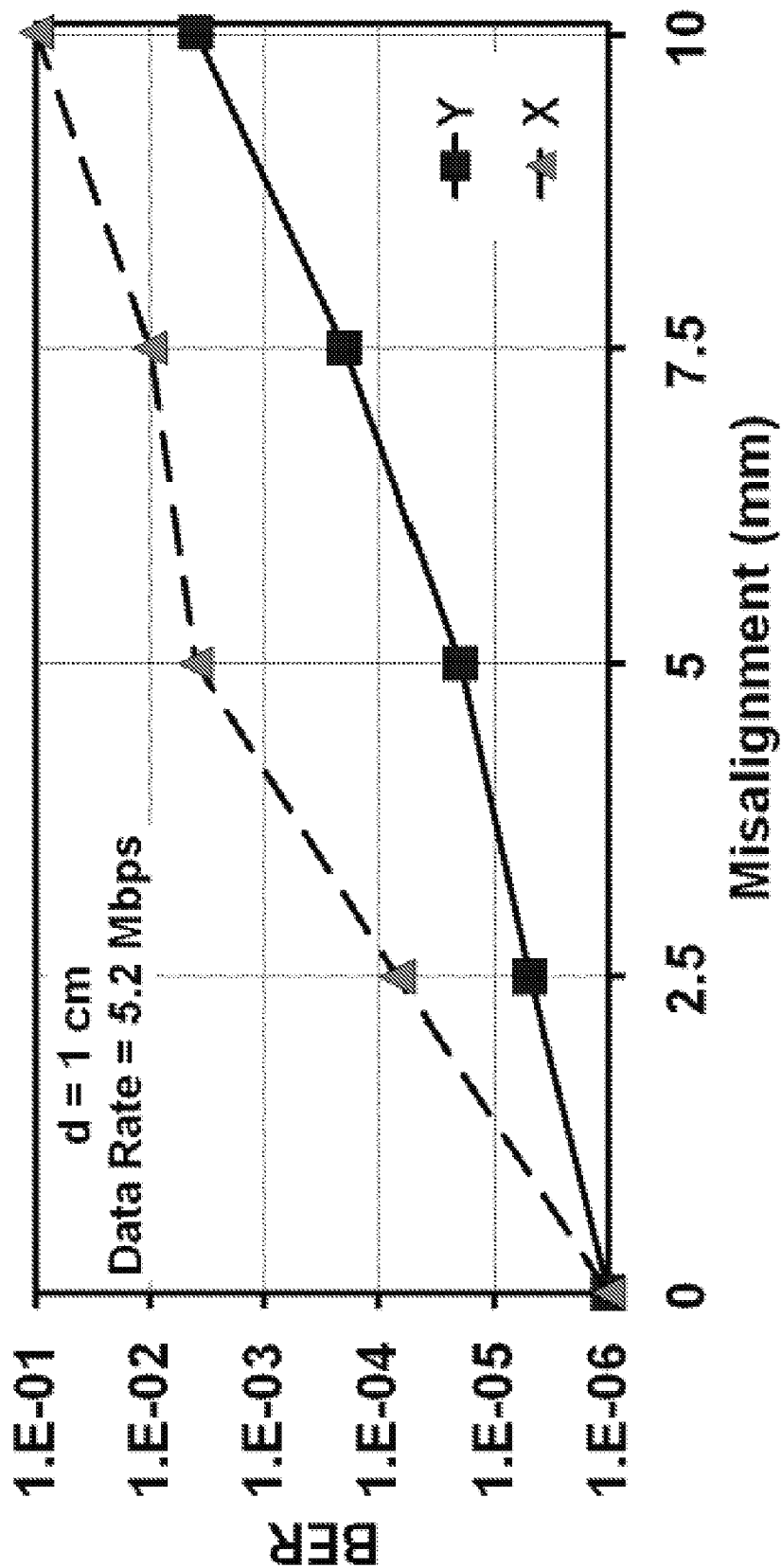
FIG. 12B provides the measured changes in BER due to coil misalignments along X and Y axes in exemplary embodiments of the present invention.

FIG. 12B provides the measured changes in BER due to coil misalignments along the X and Y axes as shown in FIG. 7 in an exemplary embodiment of the present invention. The data rate and coils' distance are kept constant at 5.2 Mbps and 1 cm, respectively. The curves in FIG. 12B illustrate that figure-8 coils can be more robust against misalignments along the Y-axis compared to the X-axis.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the International Receiving Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. It is intended that the application is defined by the claims appended hereto.

What is claimed is:

1. A pulse harmonic modulation method, comprising:
transmitting a first data initiation pulse to an input of a first resonant circuit thereby creating an oscillating waveform at an output of a second resonant circuit; and
transmitting a first modifying pulse to the input of the first resonant circuit, wherein the first modifying pulse reduces inter-symbol interference at the output of the second resonant circuit by modifying a first portion of the oscillating waveform.

2. The pulse harmonic modulation method according the claim 1, wherein the transmitting the first modifying pulse dampens the oscillating waveform.

3. The pulse harmonic modulation method according to claim 1, wherein the first modifying pulse has a predetermined first amplitude and a predetermined first time-delay.

4. The pulse harmonic modulation method according to claim 1, wherein the transmitting the first modifying pulse decreases an amplitude of the first portion of the oscillating waveform.

5. The pulse harmonic modulation method according to claim 1, wherein the transmitting the first modifying pulse increases an amplitude of the first portion of the oscillating waveform.

6. The pulse harmonic modulation method according to claim 1, wherein the first resonant circuit is implanted substantially within a body of a user.

7. The pulse harmonic modulation method according to claim 1, wherein the first resonant circuit is substantially outside a body of a user.

8. The pulse harmonic modulation method according to claim 1, further comprising transmitting a second modifying pulse to the input of the first resonant circuit, wherein the second modifying pulse modifies a second portion of the oscillating waveform at the output of the second resonant circuit.

9. The pulse harmonic modulation method according to claim 1, wherein data is transmitted from the input of the first resonant circuit to the output of the second resonant circuit at a rate of at least five megabits per second.

10. The pulse harmonic modulation method according to claim 6, wherein the second resonant circuit is substantially outside a body of a user.

11. The pulse harmonic modulation method according to claim 7, wherein the second resonant circuit is implanted substantially within a body of a user.

12. A pulse harmonic modulation system, comprising:
a first resonant circuit in communication with a second resonant circuit; and
wherein the first resonant circuit is enabled to receive a first data initiation pulse, which causes an oscillating waveform at an output of the second resonant circuit, and the first resonant circuit is enabled to receive a first modifying pulse to reduce inter-symbol interference at the output of the second resonant circuit by modifying a first portion of the oscillating waveform.

13. The pulse harmonic modulation system according to claim 12, wherein the first modifying pulse has a predetermined first amplitude and a predetermined first time-delay.

14. The pulse harmonic modulation system according to claim 12, wherein the first modifying pulse modifies the first portion of the oscillating waveform by decreasing an amplitude of the first portion of the oscillating waveform.

15. The pulse harmonic modulation system according to claim 12, wherein the first modifying pulse modifies the first portion of the oscillating waveform by increasing an amplitude of the first portion of the oscillating waveform.

16. The pulse harmonic modulation system according the claim 12, wherein the first modifying pulse modifies the first portion of the oscillating waveform by decreasing a dampening, wherein the dampening time is the time it takes the oscillating waveform to dampen below a predetermined threshold value.

17. The pulse harmonic modulation system according to claim 12, wherein the first resonant circuit is implanted substantially within a body of a user.

18. The pulse harmonic modulation system according to claim 12, wherein the first resonant circuit is substantially outside a body of a user.

19. The pulse harmonic modulation system according to claim 12, wherein a distance between the first resonant circuit and the second resonant circuit is less than about 20 millimeters.

20. The pulse harmonic modulation system according to claim 12, wherein the first resonant circuit is enabled to receive a second modifying pulse to modify a second portion of the oscillating waveform.

21. The pulse harmonic modulation system according to claim 12, wherein the system is configured to transmit data from the first resonant circuit to the second resonant circuit at a rate of at least five megabits per second.

22. The pulse harmonic modulation system according to claim 17, wherein the second resonant circuit is substantially outside a body of a user.

23. The pulse harmonic modulation system according to claim 18, wherein the second resonant circuit is implanted substantially within a body of a user.

24. A pulse harmonic modulation method, comprising:
transmitting a first data initiation pulse indicative of a data bit to an input of a first resonant circuit thereby creating an oscillating waveform at an output of a second resonant circuit; and
transmitting a first modifying pulse with a predetermined first amplitude and first time-delay to the input of the first resonant circuit, wherein the first modifying pulse reduces inter-symbol interference at the output of the second resonant circuit by modifying a first portion of the oscillating waveform at the output of the second resonant circuit,
wherein the first resonant circuit is located substantially within a body of a user and the second resonant circuit is located substantially outside a body of the user,
wherein data is transmitted from the input of the first resonant circuit to the output of the second resonant circuit at a rate of at least five megabits per second.

\* \* \* \* \*